(12) United States Patent
Jarrott et al.

(10) Patent No.: US 8,017,649 B2
(45) Date of Patent: Sep. 13, 2011

(54) FLAVONOID COMPOUNDS AND USES THEREOF

(75) Inventors: Bevyn Jarrott, Mt Martha (AU); Clive Newton May, North Fitzroy (AU); Owen Llewellyn Woodman, Victoria (AU); Gregory James Dusting, Kew (AU)

(73) Assignee: Howard Florey Institute of Experimental Physiology and Medicine, Victoria (AU)

( * ) Notice: Subject to any disclaimer, the term of this patent is extended or adjusted under 35 U.S.C. 154(b) by 811 days.

(21) Appl. No.: 11/885,736

(22) PCT Filed: Mar. 10, 2006

(86) PCT No.: PCT/AU2006/000314
§ 371 (c)(1),
(2), (4) Date: Mar. 4, 2008

(87) PCT Pub. No.: WO2006/094357
PCT Pub. Date: Sep. 14, 2006

(65) Prior Publication Data
US 2009/0130051 A1      May 21, 2009

(30) Foreign Application Priority Data
Mar. 11, 2005  (AU) ................................ 2005901214

(51) Int. Cl.
*A61K 31/352*   (2006.01)
*C07D 311/30*   (2006.01)
(52) U.S. Cl. ..................... 514/456; 549/400; 549/403
(58) Field of Classification Search .............. 549/400, 549/403; 514/456
See application file for complete search history.

(56) References Cited

U.S. PATENT DOCUMENTS

| | | |
|---|---|---|
| 3,509,026 A | 4/1970 | Sanders |
| 5,070,018 A | 12/1991 | Peters et al. |
| 5,229,116 A | 7/1993 | Edgar et al. |
| 5,360,915 A | 11/1994 | Riede et al. |
| 5,792,448 A | 8/1998 | Dubief et al. |
| 6,133,241 A | 10/2000 | Bok et al. |
| 6,180,661 B1 | 1/2001 | Eugster et al. |
| 6,329,422 B1 | 12/2001 | Fischer et al. |
| 6,471,973 B1 | 10/2002 | Perrier et al. |
| 6,495,718 B1 | 12/2002 | Schmidt |
| 6,500,846 B1 | 12/2002 | Hong et al. |
| 6,506,792 B1 | 1/2003 | Reed et al. |
| 6,555,523 B1 | 4/2003 | Prendergast |
| 7,166,640 B2 | 1/2007 | Berg |
| 7,202,272 B2 | 4/2007 | Reed et al. |
| 2001/0046963 A1 | 11/2001 | Wenzel et al. |
| 2002/0147353 A1 | 10/2002 | Van Der Vijgh et al. |
| 2003/0039619 A1 | 2/2003 | Bunger et al. |
| 2003/0055103 A1 | 3/2003 | Heinzen et al. |
| 2003/0125264 A1 | 7/2003 | Malik |
| 2003/0229065 A1 | 12/2003 | Levy et al. |
| 2004/0038914 A1 | 2/2004 | Krutmann et al. |
| 2004/0067246 A1 | 4/2004 | Msika et al. |
| 2004/0067894 A1 | 4/2004 | Carola et al. |
| 2004/0076692 A1 | 4/2004 | Van Norren et al. |
| 2004/0202624 A1 | 10/2004 | Pfluecker et al. |
| 2004/0235081 A1 | 11/2004 | Burton |
| 2004/0242503 A1 | 12/2004 | Soares Da Silva |
| 2004/0266699 A1 | 12/2004 | Porta |
| 2005/0032882 A1 | 2/2005 | Chen |
| 2005/0079235 A1 | 4/2005 | Stockfleth |
| 2005/0080021 A1 | 4/2005 | Tucker et al. |
| 2005/0080024 A1 | 4/2005 | Tucker et al. |
| 2005/0148819 A1 | 7/2005 | Noguchi et al. |
| 2005/0215493 A1 | 9/2005 | Miyake et al. |
| 2005/0226828 A1 | 10/2005 | Ishida et al. |
| 2005/0261167 A1 | 11/2005 | Chan et al. |
| 2006/0014705 A1 | 1/2006 | Howitz et al. |
| 2006/0079467 A1 | 4/2006 | Jia et al. |
| 2006/0105967 A1 | 5/2006 | Hsu et al. |
| 2006/0135445 A1 | 6/2006 | Yamazaki et al. |
| 2006/0148726 A1 | 7/2006 | Berg |
| 2006/0229358 A1 | 10/2006 | Ko |
| 2007/0037193 A1 | 2/2007 | Lin et al. |
| 2007/0059387 A1 | 3/2007 | Stockfleth |
| 2007/0099826 A1 | 5/2007 | Wong et al. |

FOREIGN PATENT DOCUMENTS

| | | |
|---|---|---|
| EP | 0 117 440 A1 | 9/1984 |
| WO | WO 95/25733 A1 | 9/1995 |
| WO | WO 98/58934 A1 | 12/1998 |
| WO | WO 99/66062 A1 | 12/1999 |
| WO | WO 00/44757 A1 | 8/2000 |
| WO | WO 01/21608 A2 | 3/2001 |
| WO | WO 03/006452 A1 | 1/2003 |
| WO | WO 03/035900 A1 | 5/2003 |
| WO | WO 2004/005243 A2 | 1/2004 |
| WO | WO 2006 094357 A1 | 9/2006 |
| WO | WO 2007 082178 A2 | 7/2007 |

OTHER PUBLICATIONS

Calias et al, Carbohydrate Research, vol. 292, p. 83-90, (1996).*
New Zealand No. 280330; New Zealand Patents Act, 1953, Complete Specification, filed Oct. 25, 1995, Publication Date Dec. 20, 1996, P.O. Journal No. 1411; "New Diosmetin Compounds, A Process for their Preparation and Pharmaceutical Compositions Containing Them"; (78 pgs).
New Zealand No. 314678; New Zealand Patents Act 1953, Complete Specification, filed Apr. 24, 1997, Publication Date Dec. 23, 1998, Journal No. 1435; "New Acids and Esters of Diosmetin and Pharmaceutical Compositions Containing Them"; (32 pgs).

(Continued)

*Primary Examiner* — Bernard Dentz
(74) *Attorney, Agent, or Firm* — Nixon & Vanderhye

(57) ABSTRACT

Novel flavonoid compounds having anti-oxidant activity are described. The compounds and compositions have been shown to exhibit anti-oxidant properties and are particularly useful in the treatment of ischemia and reperfusion injuries. The invention also describes a method to chemically synthesize such flavonoid compounds and test their efficacy. Such compounds and corresponding pharmaceutically acceptable derivatives and/or salts have uses in the areas of pharmaceuticals, nutraceutical, and veterinary applications.

36 Claims, 19 Drawing Sheets

OTHER PUBLICATIONS

New Zealand No. 241633; New Zealand Patents Act 1953, Complete Specification, filed May 17, 1992, Publication Date Jun. 27, 1994, Journal No. 1381; "Benzopyran Phenol Derivatives for Use as Antibacterial, Antiviral or Immunostimulating Agents"; (105 pgs).

New Zealand No. 328858; New Zealand Patents Act 1953, Complete Specification, filed Sep. 26, 1997, Publication Date Jan. 26, 1998, Journal No. 1424; "New Flavone Compounds, Process for Preparing them and Pharmaceutical Compositions Containing Them"; (34 pgs).

Wang, Sheng, et al; "3',4'-dihydroxyflavonol reduces infract size and injury associated with myocardial ischaemia and reperfusion in sheep"; British Journal of Pharmacology; vol. 142; pp. 443-452 (2004).

STN File CA, Abstract 127:290447 & H. Martini et al; Mycological Research (1997).

STN File CA, Abstract 127:229311 & A.F. Barrero et al; Fitoterapia (1997).

CAS Registry No. 102080-28-4, May 10, 1986.

CAS Registry No. 72994-98-0, Nov. 16, 1984.

CAS Registry No. 733016-22-3, Aug. 26, 2004.

Hergert, H.L., et al; "The Infrared Spectra of Lignin and Related Compounds. I. Characteristic Carbonyl and Hydroxyl Frequencies of Some flavanones, Flavones, Chalcones and Acetophenones[1]"; Journal of the American Chemical Society; vol. 75, pp. 1622-1625 (1953).

Kamkhalia, N.H., et al; "Synthesis of (±) Fustin and its Derivatives"; Current Science vol. 32(3), pp. 112-113 (1963).

Dudakova, T.V., et al; "Phosphorylation of 3-hydroxy- and 5,7-dihydroxyflavones with hexaethylphosphorous triamide"; Russian Chemical Bulletin, International Edition, vol. 53, No. 12; pp. 2810-2815 (2004).

Database Caplus, Chemical Abstracts Service, Columbus, OH; Olivero-Verbel, J., et al; "Structure-Activity Relationships for the Anti-HIV Activity of Flavonoids", Journal of Chemical Information and Computer Sciences, vol. 45, No. 5, pp. 1241-1246, (2002), XP002592707 (abstract).

Database Caplus, Chemical Abstracts Service, Columbus, OH; Reichel, L., et al; "o-(Aminoacyl)hydroxyflavones"; Zeitschrift Fuer Chemie; vol. 6, No. 7, 260 Coden: Zeceal (1966), XP002599348 (abstract).

Database Caplus, Chemical Abstracts Service, Columbus, OH; Calias, P., et al; "Synthesis of inositol 2-phosphate-quercetin conjugates"; Carbohydrate Research; vol. 292, 83-90 Coden: CRBRAT (1996), XP002599349 (abstract).

Kim, J., et al; "Synthesis of Naringenin Amino Acid Esters as Potential CDK2 Inhibitors"; Bull. Korean Chem. Soc., vol. 26, No. 12, pp. 2065-2068 (2005), XP002592826.

Database Caplus, Chemical Abstracts Service, Columbus, OH, Wu, X., et al; "Syntheses of carbamate derivatives of quercetin by reaction with amino acid ester isocyanates"; Letters in Organic Chemistry; vol. 2, No. 6, pp. 535-538 Coden: LOCEC7 (2005), XP002599351 (abstract).

Cash, C.D., "Are the Reactive Oxygen-Derived Species (ROS) Interactive Properties of the Many Therapeutic Drugs from Various Categories Pertinent to their Beneficial Effects?"; Gen Pharmac., vol. 28, No. 2, pp. 169-175 (1997), XP001050580.

Hergert, H.L., et al; "The Infrared Spectra of Lignin and Related Compounds. I. Characteristic Carbonyl and Hydroxyl Frequencies of Some Flavanones, Flavones, Chalcones and Acetophenones"; Department of Chemistry, Oregon State College, and the Oregon Forest Products Laboratory; vol. 75, pp. 1622-1625 (1952).

Devanathan, T.; "The Hydrogen Bonding Energies from Near Ultra-Violet Absorption Spectra in p-Bromo-Phenol and o-Hydroxy Biphenyl"; Letters to the Editor (Current Science), No. 3, pp. 112-113 (1963).

Martini, H., et al; "Increased antifungal activity of 3- and 7-hydroxyflavone against Cladosporium herbarum and Penicillium glabrum through ester formation"; Mycol. Res.; vol. 101, No. 8, pp. 920-922 (1997).

CAS Registry RN 102080-28-4, Answer 1 (2010) ACS on STN; CAS Registry RN 733016-22-3, Answer 1 (2010) ACS on STN, (1 pg).

Barrero, A.F., et al; "Cytotoxic Activity of Flavonoids from Carthamus arborescens, Ononins natrix ssp. Ramosissima and Centaurea malacitana"; Fitoterapia, vol. LXVIII, No. 3; pp. 281-283 (1997).

* cited by examiner

FLAVONOID COMPOUNDS AND USES THEREOF

CROSS-REFERENCE TO RELATED APPLICATIONS

This application is the U.S. National Phase of International Application PCT/AU2006/000314, filed 10 Mar. 2006, which designated the U.S. PCT/AU2006/000314 claims priority to Australian Application No. 2005901214, filed 11 Mar. 2005. The entire content of these applications are incorporated herein by reference.

FIELD OF THE INVENTION

The present invention relates to novel compounds, compositions containing these compounds, methods for their synthesis, and uses of these compounds. In particular, the present invention relates to flavonoid compounds, methods of synthesizing the flavonoid compounds, compositions containing the flavonoid compounds and methods of their use.

BACKGROUND OF THE INVENTION

Prompt reperfusion of ischemic tissue is critical for restoring normal function. However, this return of blood flow can paradoxically produce a progressive destruction of reversibly damaged cells, thereby leading to tissue dysfunction and infarction. This "reperfusion injury" has multifactorial causes of disease but appears to be strongly associated with an inflammatory response; with the return of blood flow, several inflammatory processes may occur to potentiate ischemic injury, including leukocyte adhesion and infiltration and the release of reactive oxidative species (ROS) such as oxygen free radical species and peroxides, for example $H_2O_2$.

Much of this inflammatory response appears to be mediated by interleukins (ILs), a multifunctional subclass of cytokines. Leukocytes (white blood cells) also appear to play a critical role in reperfusion injury. In addition to injuring endothelium and neurons, leukocytes can obstruct the microcirculation directly. This leukocyte capillary plugging also may be the major mechanism of the "no-reflow phenomenon." Thus areas of parenchyma that are still viable when blood flow returns are not reperfused adequately and ultimately die. Myocardial ischaemia in particular causes extensive capillary plugging.

Ischaemia, and particularly reperfusion, tend to promote an increased release of ROS's from leukocytes which leads to further tissue damage. One of the most damaging types of free radicals is superoxide anions which act to impair endothelial function and the activity of nitric oxide (NO). This further worsens the capillary plugging process because NO has been shown to inhibit platelet aggregation and to prevent leukocyte adherence to the endothelium.

The degree of tissue recovery achieved after ischaemia and reperfusion depends on the nature of the tissue and the severity of the damage.

Ischaemia can be caused by a variety of conditions. For example, acute incidents such as stroke, myocardial infarction or mechanical trauma, and chronic conditions such as atherosclerosis, peripheral vascular disease and diabetes can cause ischaemia. Hypertension is another type of disorder that can lead to ischaemia.

Following an acute incident such as a heart attack caused by a blocked coronary artery, various drugs are delivered intravenously to the heart attack victim to assist in removing any blood vessel obstruction thus re-establishing blood flow leading to reperfusion of tissues. However, this type of treatment is not directed to preventing or ameliorating the tissue damage associated with reperfusion. Creating an environment for reperfusion to occur and re-establish the supply of oxygen to tissue can lead to increased tissue damage by increasing free radical production.

In this respect the conventional treatments for subjects exhibiting ischaemia or at risk of ischaemia are inadequate.

It has been suggested that various substances improve vascular health and function, and that in populations with a diet high in fruits and vegetables there is a lower incidence of coronary arterial disease. This effect has been linked to the beneficial effects of flavonoids, which are polyphenolic compounds that are found in both fruits and vegetables.

Flavonoids are a very large and widespread group of plant derived compounds which are thought to exhibit a number of biological effects including reducing plasma levels of low density lipoproteins, inhibiting platelet aggregation, scavenging free radicals and reducing cell proliferation as well as modulating vascular tone.

A vast number of flavonoids have been identified and differ from one another in the orientation of the hydroxylation or methylation, the position of the benzenoid substituent, the degree of unsaturation and the types of substituents attached. The general three ring structure (A, B and C rings) of many flavonoids are based on the structure of 2-phenyl-4H-1-benzopyran-4-one.

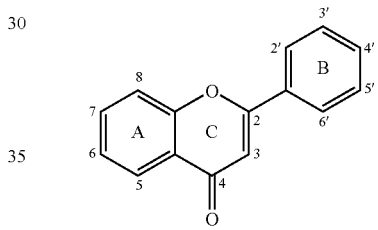

Flavonoid basic structure

For example, the synthetic flavonoid, 3,4'-dihydroxy flavonol (DiOHF) has a hydroxyl group at the 3,3'- and 4' positions and has been demonstrated to reduce Infarct and injury associated with myocardial ischaemia and reperfusion during in vitro studies (Shen Wang, Gregory Dusting, Clive May and Owen Woodman, British Journal of Pharmacology (2004) 142, 443-452).

However, the pharmacokinetics of many flavonoids has severely limited their therapeutic usefulness. Synthetic flavonoids tend to be highly lipid soluble molecules and therefore tend to have poor water solubility leading to a difficulty in administration as a therapeutic agent. These characteristics limit their applicability to therapies where acute parenteral administration is desirable, for example in vasodilation therapies.

Given the above identified problems, there remains a need for the development of synthetic flavonoid derivatives with improved aqueous solubility and pharmacokinetics when compared to known flavonoids.

SUMMARY OF THE INVENTION

According to a first aspect, the present invention provides a pharmaceutically and/or veterinary composition comprising a pharmaceutically and/or veterinarily acceptable carrier or diluent together with at least one compound of the general Formula I:

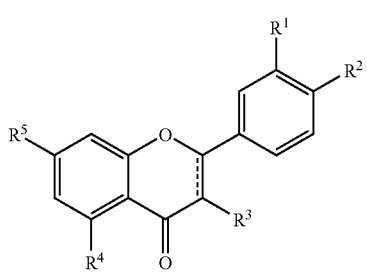

in which:
= denotes a single or double bond; and
$R^1, R^2, R^3, R^4, R^5$ are independently selected from H, OH or a group according to Formula (Ia):

—O-L-D-E    (Ia)

in which
O is oxygen;
L is a linker group which is covalently linked to the oxygen and D, if present, or is covalently linked to the oxygen and E, or is absent;
D is a spacer group having a chain length equivalent to about 1 to 20 carbon atoms, or is absent; and
E is a solubilizing group;
provided that at least one of $R^1, R^2, R^3, R^4, R^5$ is other than H or OH.

Preferably, E is selected from an ester, a carboxylic acid, sulfonic acid, phosphonic acid, phosphate ester, sulfamate, sulfonic ester, phosphamate, phosphonate ester, sulphonate, zwitterionic specie, amino acid, amino phosphonate, acyclic amine, cyclic amine, quaternary ammonium cation, polyethylene glycol, oligosaccharide or dendrimer.

In one preferred embodiment, E is a selected from an ester, carboxylic acid, sulfonic acid, phosphonic acid, phosphate ester, polyethylene glycol, oligosaccharide or dendrimer.

Preferably E is selected from an ester, carboxylic acid or phosphate ester.

In a particular preferred embodiment, E is group according to Formula (Ib):

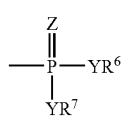    (Ib)

wherein
W is O, NH, S, O—, NH⁻ or S⁻; and
X is H, a mono- or divalent cationic salt, or an ammonium canonic salt.
Preferably, W is O and/or X is H.
In another embodiment, E is an ester according to the Formula (Ic):

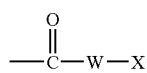    (Ic)

wherein
Q is a substituted or unsubstituted alkylene, alkenylene, alkynylene, optionally interrupted by one or more heteroatom(s);
W is O, NH, S, O⁻, NH⁻, or S⁻; and
X is H, substituted or unsubstituted alkyl, alkylbenzyl, a mono- or divalent cationic salt, or an ammonium cationic salt.

Preferably, Q is a substituted or unsubstituted lower alkylene.

In another embodiment, E is a phosphate ester according to the Formula (Id):

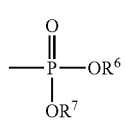    (Id)

wherein
Y is O, NH, S, O⁻, NH⁻, or S⁻;
Z Is O or S; and
$R^6$ and $R^7$ are independently selected from H, substituted or unsubstituted alkyl, a mono- or divalent cationic salt, or an ammonium canonic salt.

Preferably Y and Z are O.

In another embodiment, at least one of $R^1, R^2, R^3, R^4$ and $R^5$ is phosphate ester according to the formula (Ie):

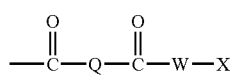    (Ie)

wherein $R^6$ and $R^7$ are independently selected from H, a mono- or divalent cationic salt, or an ammonium cationic salt.

In one embodiment, L is present and selected from —CO—, ester, phenol, phosphonate ester, carbamate, carbonate or a Mannich base. In a more preferred embodiment, L is —CO—.

In another embodiment, D present and selected from substituted or unsubstituted alkylene, alkenylene, alkynylene, optionally interrupted by one or more heteroatom(s), aryl, heteroaryl, cycloalkyl or heterocycloalkyl.

In a preferred embodiment D is a substituted or unsubstituted alkylene, optionally interrupted by one or more heteroatom(s). Preferably, a lower alkylene.

In another aspect, the present invention provides a pharmaceutically and/or veterinary composition comprising a pharmaceutically and/or veterinarily acceptable carrier or diluent together with at least one compound of the general Formula II:

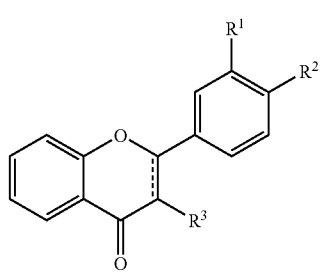    II wherein
= denotes a single or double bond; and
$R^1, R^2$ and $R^3$ are as specified above.

In yet another aspect, the present invention provides a pharmaceutically and/or veterinary composition comprising a pharmaceutically and/or veterinarily acceptable carrier or diluent together with at least one compound of the general Formula III:

III

*[Chemical structure: flavone with 3',4'-dihydroxy substitution and R³ at position 3]* wherein R3 is specified above.

In yet another aspect, the present invention provides a pharmaceutically and/or veterinary composition comprising a pharmaceutically and/or veterinarily acceptable carrier or diluent together with at least one compound of the general Formula IV:

IV

*[Chemical structure: flavone with 3',4'-dihydroxy substitution and O—C(=O)—Q—C(=O)—O—X at position 3]* wherein
Q is substituted or unsubstituted alkylene, optionally interrupted by one or more heteroatom(s)
X is H, a mono- or divalent cationic salt, or an ammonium cationic salt.

Preferably Q is substituted or unsubstituted lower alkylene, optionally interrupted by one or more heteroatom(s).

In another aspect, the present invention provides a compound selected from the group 3-(Benzyloxycarbonylbutylcarbonyloxy)flavone; 3-Hydroxyflavone 3-hemiadipate; 4'-(Benzyloxy)-3-(benzyloxycarbonylbutylcarbonyloxy) flavone; 4'-Hydroxyflavone 3-hemiadipate; 3',4'-Dibenzyloxy-3-(benzyloxycarbonylbutylcarbonyloxy) flavone; 3',4'-Dihydroxyflavone 3-hemiadipate; 3,4'-Di-(benzyloxycarbonylbutylcarbonyloxy)flavone; Flavone 3,4'-bis(hemiadipate); 3,7-Di-(benzyloxycarbonylbutylcarbonyloxy)flavone; 3,7-Dihydroxyflavone 3,7-bis(hemiadipate); 4'-Hydroxy-3-Hydroxyflavone-3-quaternary ammounium ester; 4'-(Benzyloxy)-3-(dibenzyloxyphosphoryloxy)flavone and 3-Hydroxyflavone-3-phosphate disodium salt.

In another aspect, the present invention provides a pharmaceutically and/or veterinary composition comprising a pharmaceutically and/or veterinarily acceptable carrier or diluent together with at least one compound selected from the group comprising 3-(Benzyloxycarbonylbutylcarbonyloxy) flavone; 3-Hydroxyflavone 3-hemiadipate; 4'-(Benzyloxy)-3-(benzyloxycarbonylbutylcarbonyloxy)flavone; 4'-Hydroxyflavone 3-hemiadipate; 3',4'-Dibenzyloxy-3-(benzyloxycarbonylbutylcarbonyloxy)flavone; 3',4'-Dihydroxyflavone 3-hemiadipate; 3,4'-Di-(benzyloxycarbonylbutylcarbonyloxy)flavone; flavone 3,4'-bis(hemiadipate); 3,7-Di-(benzyloxycarbonylbutylcarbonyloxy)flavone; 3-(Dibenzyloxyphosphoryloxy)flavone; 3,7-Dihydroxyflavone 3,7-bis(hemiadipate); 4'-Hydroxy-3-Hydroxyflavone-3-quaternary ammonium ester; Flavone-3-phosphate disodium salt; 4'-(Benzyloxy)-3-(dibenzyloxyphosphoryloxy) flavone or 3-Hydroxyflavone-3-phosphate disodium salt.

In yet a further aspect, the present invention provides a method of preventing and/or treating a disease(s) in a subject associated with the presence of reactive oxidative species (ROS), the method comprising:
administering an effective amount of at least one compound specified above.

Preferably, the subject in need of such treatment is at risk of developing ischaemia. More preferably, the subject is suffering ischaemia and/or reperfusion injury as a result of an acute or chronic condition.

In a particular embodiment, the chronic condition is selected from cancer, cerebrovascular, disease, pulmonary vascular disease, atherosclerosis, artery disease, congestive heart disease, coronary disease, peripheral vascular disease, diabetes, hypertension, migraine, burns, chronic obstructive pulmonary disease and retinal vascular disease.

In another embodiment, the acute condition is selected from stroke, myocardial infarction, mechanical trauma resulting from crush injury or surgery. Preferably the surgery is vascular surgery. More preferably, the vascular surgery is heart bypass and/or transplant surgery.

In a particular embodiment, the compound is administered to the subject before and/or during the surgery.

In another aspect, the present invention provides a method of preventing, delaying the onset of and/or slowing the progression of atherosclerosis and/or coronary heart disease in a subject comprising
administering an effective amount of at least one compound specified above.

In yet a further aspect, the present invention provides a therapeutic and/or prophylactic method of preventing and/or treating a disease(s) in a subject associated with the presence of reactive oxidative species (ROS), the method comprising:
administering an effective amount of at least one compound specified above.

In yet a further aspect, the present invention provides a method of preventing and/or at least ameliorating the damage to a subject caused by ischaemia and/or reperfusion injury, the method comprising
administering an effective amount of at least one compound specified above.

In yet a further aspect, the present invention provides a method of preventing and/or at least ameliorating damage to a subject caused by the administration of a therapeutic agent the method comprising co-administering to a subject:
i) a therapeutic agent: and
ii) administering an effective amount of at least one compound specified above.

Preferably the therapeutic agent is an oxidative therapeutic agent.

In a particular embodiment the therapeutic agent is an anticancer agent Preferably the anticancer agent is anthracycline and its derivatives.

In particular embodiments, the compound is administered orally, topically, subcutaneous, parenterally, intramuscular, intra-arterial and/or intravenously.

In another aspect, the present invention provides for the use of a compound as specified above for the preparation of a medicament.

In another further aspect, the present invention provides a compound of the general Formula I:

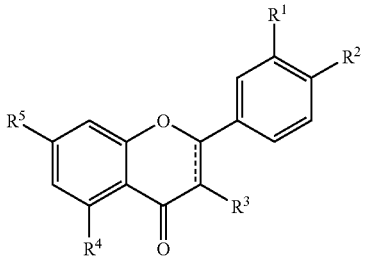

wherein:
══ denotes a single or double bond; and
$R^1$, $R^2$, $R^3$, $R^4$, $R^5$ are independently selected from H, OH or a group according to Formula (Ia):

 —O-L-D-E (Ia)

wherein:
O is oxygen;
L is a linker group which is covalently linked to the oxygen and D, if present, or is covalently linked to the oxygen and E, or is absent;
D is a spacer group having a chain length equivalent to about 1 to 20 carbon atoms, or is absent; and
E is a solubilizing group;
provided that at least one of $R^1$, $R^2$, $R^3$, $R^4$, $R^5$ is other than H or OH,
with the proviso that the compound is not flavone, 3'-hydroxy-, acetate; Flavone, 4'-hydroxy-, acetate; Flavone, 3-hydroxy-, acetate; (±)-41-Acetoxyflavanone; Flavanone, 3,4',7-trihydroxy-, 3-acetate; 4H-1-Benzopyran-4-one, 3,7-bis(acetyloxy)-2,3-dihydro-2-phenyl-, (2R-trans)-; 4H-1-Benzopyran-4-one, 7-(acetyloxy)-2-[4-(acetyloxy)phenyl]-2,3-dihydro-, (±); (+)-4',7-Diacetoxyflavanone; (2S,3S)-3,7-Dihydroxyflavanone diacetate; Flavanone, 3,4'-dihydroxy-, diacetate; Flavanone, 3',4'-dihydroxy-, diacetate; Flavanone, 3,7-dihydroxy-, diacetate; 4H-1-Benzopyran-4-one, 3,7-bis(acetyloxy)-2-(3,4-dihydroxyphenyl)-2,3-dihydro-, (2R-trans)-; Flavone, 3,3'-dihydroxy-, diacetate; Flavone, 4',7-dihydroxy-, diacetate; Flavone, 3,7-dihydroxy-, diacetate; Flavone, 3,3',7-trihydroxy-, triacetates; Flavone, 3,3',4'-trihydroxy-, triacetate; 4H-1-Benzopyran-4-one, 7-(acetyloxy)-2-[3,4-bis(acetyloxy)phenyl]-; Flavone, 3,4',7-trihydroxy-, triacetate; Flavanone, 3',4',7-trihydroxy-, triacetate; 4H-1-Benzopyran-4-one, 7-(acetyloxy)-2-[3,4-bis(acetyloxy)phenyl]-2,3-dihydro-, (S)—; Flavanone, 3,4',7-trihydroxy-, triacetate; Flavanone, 3,4',7-trihydroxy, triacetate, trans-(t)-; 4H-1-Benzopyran-4-one, 3,7-bis(acetyloxy)-2-[3,4-bis(acetyloxy)phenyl]-; Fustin, tetraacetate; 4H-1-Benzopyran-4-one, 3,7-bis(acetyloxy)-2-[3,4-bis(acetyloxy)phenyl]-2,3-dihydro-, (2R-trans)-; 4H-1-Benzopyran-4-one, 3,7-bis(acetyloxy)-2-[3,4-bis(acetyloxy)phenyl]-2,3-dihydro-, trans-; Flavanone, 3,3',4',7-tetrahydroxy-, tetraacetate; 4H-1-Benzopyran-4-one, 3-(1-oxopropoxy)-2-phenyl-; Propanoic acid, 2-methyl-; 4-oxo-2-phenyl-4H-1-benzopyran-3-yl ester; Propanoic acid, 2,2-dimethyl-, 4-oxo-2-phenyl-4H-1-benzopyran-3-yl ester; Benzeneacetic acid, 4-oxo-2-phenyl-4H-1-benzopyran-3-yl ester; Benzenepropanoic acid, 4-oxo-2-phenyl-4H-1-benzopyran-3-yl ester; Benzeneacetic acid, a-phenyl-, 4-oxo-2-phenyl-4H-1-benzopyran-3 yl ester; Phosphorothioic acid, o-[4-[3-[(diethoxyphosphinothioyl)oxy]-4-oxo-4H-1-benzopyran-2-yl]phenyl] o,o-diethyl ester; Phosphorothioic acid, o-[3-[3-[(diethoxyphosphinothioyl)oxy]-4-oxo-4H-1-benzopyran-2-yl]phenyl]o,o-diethyl ester; Phosphoric acid, diethyl 4-(4-oxo-4H-1-benzopyran-2-yl)phenyl ester; 4H-1-Benzopyran-4-one, 2-phenyl-3-(phosphonooxy)-; Flavone, 3-hydroxy-, dihydrogen phosphate diammonium salt; 4H-1-Benzopyran-4-one, 2-phenyl-3-(phosphonooxy)-, magnesium salt (1:1), pentahydrate; 4H-1-Benzopyran-4-one, 2-[3-hydroxy-4-(phosphonooxy)phenyl]-; 3',4'-dihydroxyflavone-4'-phosphate; 3',4'-dihydroxyflavone-4'-β-D-glucopyranoside sodium salt; 3',4'-dihydroxyflavone-4'-β-D-ribofluranoside sodium salt;
and pharmaceutically and/or veterinarily acceptable salts or solvates thereof.

Preferably, $R^1$, $R^2$, $R^3$, $R^4$ and $R^5$ are as specified above.

In another aspect, the present invention provides a compound according to the general Formula (II):

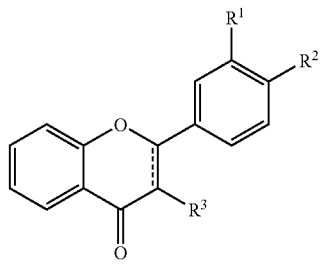

wherein
══ denotes a single or double bond; and
$R^1$, $R^2$ and $R^3$ are as specified above.

In yet another aspect, the present invention provides a compound according to the general Formula (III):

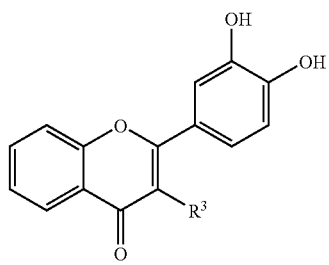

wherein $R^3$ is specified above.

In yet a further aspect, the present invention provides a compound according to the general Formula (IV):

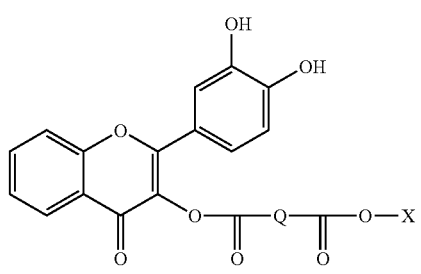

wherein
Q is substituted or unsubstituted alkylene, optionally interrupted by one or more heteroatom(s)
X is H, a mono- or divalent cationic salt, or an ammonium cationic salt.

Preferably, Q is substituted or unsubstituted lower alkylene, optionally interrupted by one or more heteroatom(s).

In another aspect, the present invention provides a compound according to the general Formula V:

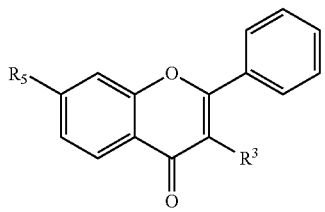

(V)

wherein $R^3$ and $R^5$ are specified above.

In another aspect, the present invention provides a method for synthesizing compounds as specified above.

According to yet another aspect, the present invention provides compounds of general Formula:

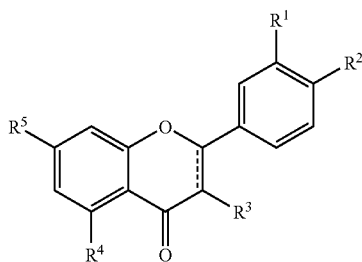

in which:
= denotes a single or double bond; and
$R^1$, $R^2$, $R^3$, $R^4$, $R^5$ which are independently selected from H, OH, substituted or unsubstituted alkoxy, aryloxy, esters, carbonate esters, ethers, phosphate esters and α-acyloxyalkyl ethers provided that at least one of $R^1$, $R^2$, $R^3$, $R^4$, $R^5$ is other than H or OH;
and pharmaceutically acceptable salts or solvates thereof.

Preferably at least $R^3$ is selected from substituted or unsubstituted esters, carbonate esters, ethers, phosphate esters and α-acyloxyalkyl ethers.

Preferably at least one of $R^1$, $R^2$, $R^3$, $R^4$ or $R^5$ is selected from:
i) phosphate having the general formula

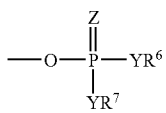

wherein Y is O, NH, S, O⁻, NH⁻, or S⁻;
Z is O or S; and
each of $R^6$ and $R^7$ are independently selected from substituted or unsubstituted alkyl, H, a mono- or divalent cationic salt, or an ammonium cationic salt;

ii) ester having the general formula

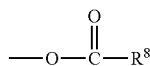

where $R^8$ is a substituted or unsubstituted lower alkyl, lower alkylalkoxy;

iii) ester having the general formula

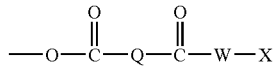

where Q is a substituted or unsubstituted lower alkylene, lower alkenyl, and alkynyl;
W is O, NH, S, O⁻, NH⁻, or S⁻; and
X is H, substituted or unsubstituted alkyl, alkylbenzyl, a mono- or divalent cationic salt, or an ammonium cationic salt, and pharmaceutically acceptable salts or solvates thereof.

In particular embodiments of the invention, Y and Z are both O.

In one embodiment, the present invention provides compounds of general Formula:

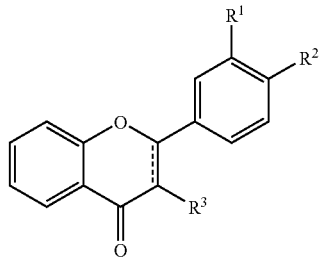

in which:
= denotes a single or double bond; and
$R^1$, $R^2$ or $R^3$ which are independently selected from H, OH, substituted or unsubstituted alkoxy, aryloxy, esters, carbonate esters, ethers, phosphate esters and α-acyloxyalkyl ethers provided that at least one of $R^1$, $R^2$ or $R^3$ is other than H or OH;
and pharmaceutically acceptable salts or solvates thereof.

Preferably at least one of $R^1$, $R^2$ or $R^3$ is selected from:
i) phosphate having the general formula

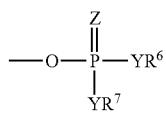

wherein Y is O, NH, S, O⁻, NH⁻, or S⁻;
Z is O or S; and
each of $R^6$ and $R^7$ are independently selected from substituted or unsubstituted alkyl, H, a mono- or divalent cationic salt, or an ammounium cationic salt;

ii) ester having the general formula

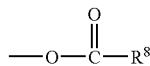

where $R^8$ is a substituted or unsubstituted lower alkyl, lower alkylalkoxy;

iii) ester having the general formula

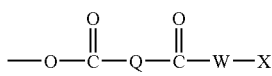

where Q is a substituted or unsubstituted lower alkylene, lower alkenylene, alkynylene, optionally interrupted by one or more heteroatom(s);

W is O, NH, S, O⁻, NH⁻, or S⁻; and

X is H, substituted or unsubstituted alkyl, alkylbenzyl, a mono- or divalent cationic salt, or an ammonium cationic salt;

and pharmaceutically acceptable salts or solvates thereof.

Preferably $R^1$ is H or OH;

$R^2$ is H or OH; and $R^3$ is selected from

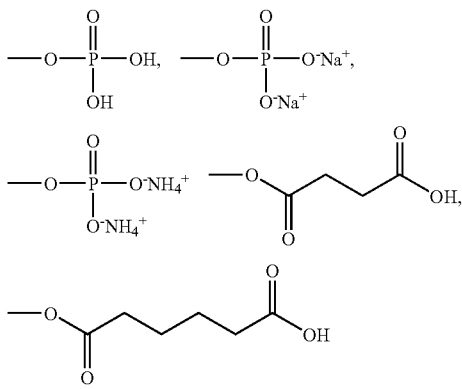

In another embodiment, the present invention provides a compound of general Formula:

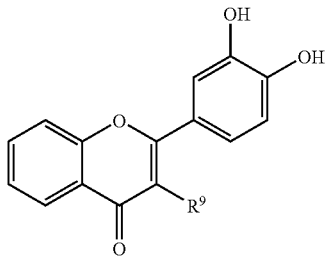

in which $R^9$ is substituted or unsubstituted alkoxy, aryloxy, ester, carbonate ester, ether, or a group according to formula

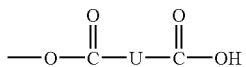

where U is substituted or unsubstituted alkylene, optionally interrupted by one or more heteroatom(s).

In another embodiment, the present invention provides a compound of general Formula:

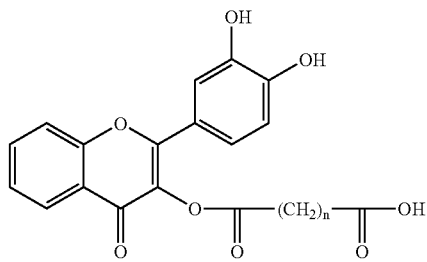

where n is an integer from 2 to 6, preferably n is 4.

The formulae given herein are intended to extend to all possible geometric and optical isomers as well as racemic mixtures thereof.

In another aspect, the present invention provides methods for synthesizing compounds in accordance with Formula I, Formula II, Formula III or Formula IV, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

In another aspect, the present invention provides a pharmaceutical and/or a veterinary composition comprising a pharmaceutically and/or veterinarily acceptable carrier or diluent together with at least one compound in accordance with Formula I, Formula II, Formula III or Formula IV, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

According to another aspect of the present invention, there is provided a method of preventing and/or at least ameliorating damage to a subject caused by the administration of a therapeutic agent, the method comprising co-administering to a subject:

i) a therapeutic agent; and ii) an effective amount of at least one compound in accordance with Formula I, Formula II, Formula III, Formula IV, or Formula V, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

In yet a further aspect, the present invention provides a method of preventing and/or treating a disease(s) associated with the presence of reactive oxidative species (ROS), the method comprising administering an effective amount of at least one compound in accordance with Formula I, Formula II, Formula III, Formula IV, or Formula V, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

In yet a further embodiment, the present invention provides a method of preventing and/or treating a disease(s) associated with the presence of reactive oxidative species (ROS), the method comprising administering an effective amount of at least one compound in accordance with Formula I, Formula II, Formula III or Formula IV, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

Typically the subject in need of such treatment will be a person at risk of developing ischaemia. Alternatively, the subject may be a person who is currently suffering ischaemia and/or reperfusion as a result of an acute or chronic condition.

In yet a further aspect, the present invention provides a method of preventing and/or at least ameliorating the damage to a subject caused by ischaemia and/or reperfusion, the method comprising administering an effective amount of at least one compound an effective amount of at least one compound in accordance with Formula I, Formula II, Formula IE or Formula IV, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

Preferably the solubilizing group renders the compound at least partially soluble, and more preferably, totally soluble in aqueous solution, preferably water.

Preferably the compounds of the invention have at least one in vivo enzyme cleavable substituent.

Preferably the in vivo enzyme cleavable substituent is an ionisable group at physiological pH.

|  | Maximum Contraction (percent 3 mM $Ca^{2+}$) |
|---|---|
| Control | 101 ± 1 |
| DiOHF3HA $10^{-4}$M | 101 ± 1 |
| DiOHF3HA $10^{-4}$M + BuCHE | 35 ± 6 |
| DiOHF $10^{-4}$M | 18 ± 2 |

Figure 15:
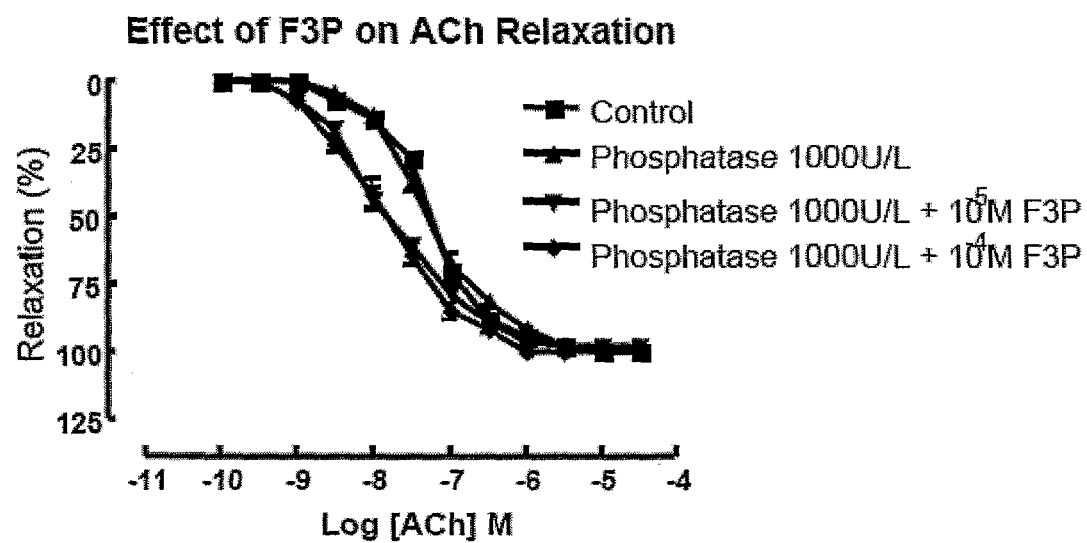

FIG. 15 illustrates the effect of phosphatase(1000 U/L) and flavone-3-phosphate, (F3P) ($10^{-5}$ M-$10^{-4}$ M) with phosphatase on concentration response curves to ACh in endothelium intact aortic rings from rats (n=5). The relaxant response to ACh did not appear to be effected by the phosphatase alone, however relaxant responses to ACh were enhanced in the presence of the F3P with phosphatase at both concentrations tested when compared to control rings.

|  | $pEC_{50}$ | $R_{max}$ |
|---|---|---|
| Control | 7.31 ± 0.03 | 100 ± 3 |
| Phosphatase $10^{-4}$M (P) | 7.30 ± 0.04 | 100 ± 1 |
| F3P $10^{-5}$M + P | 7.80 ± 0.06 | 100 ± 1 |
| F3P $10^{-4}$M + P | 7.70 ± 0.07 | 100 ± 1 |

Figure 16:
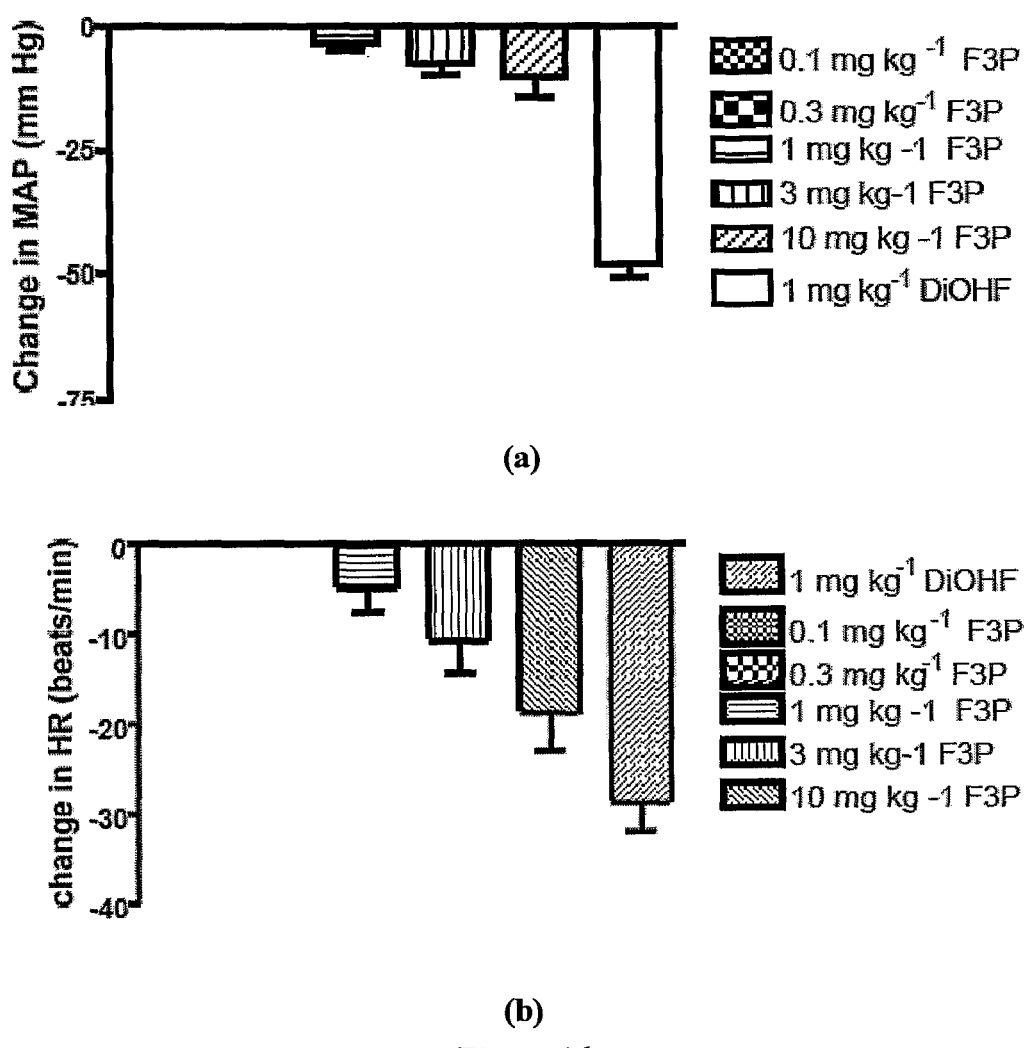

FIG. 16a illustrates the dose-dependent decreases in MAP (mm Hg) in response to F3P and DiOHF in anaesthetised rats.

FIG. 16b illustrates the dose-dependent decrease in HR (beats/min) in response to F3P and DiOHF in anaesthetised rats.

Figure 17:
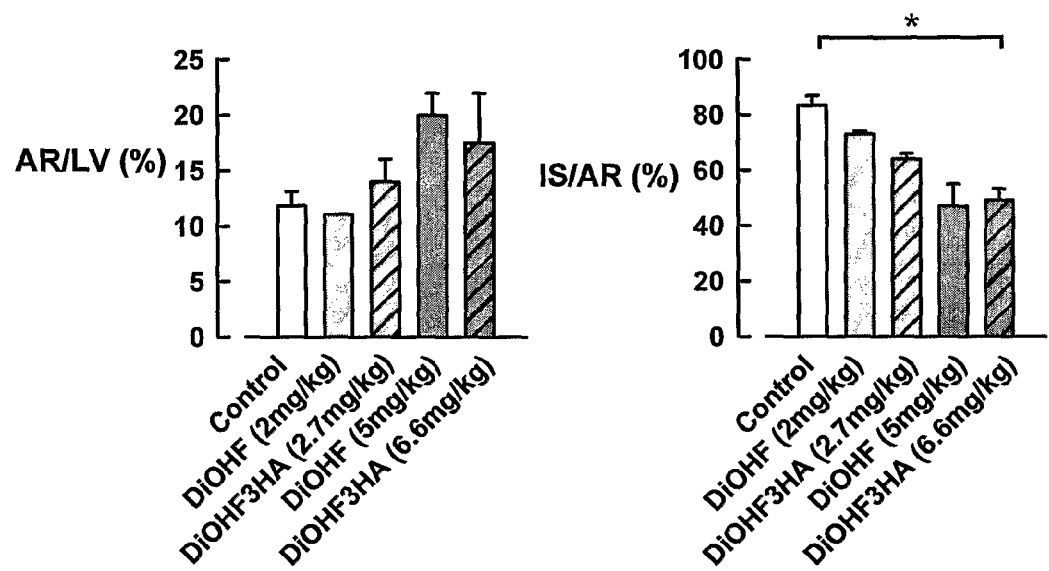

FIG. 17 illustrates the area of myocardium at risk (left panel) and myocardial infarct size (right panel) in Control (n=4), DiOHF (2 mg/kg, n=2 and 5 mg/kg, n=3) and DiOHF3HA (2.7 mg/kg, n=3 and 6.6 mg/kg, n=4) treated groups of anaesthetised sheep. AR/LV %=area at risk expressed as a percentage of total left ventricular volume. IS/AR %=infarct size expressed as a percentage of the area of myocardium at risk. * indicates significant difference in infarct size between Control and Adipate (6.6 mg/kg)-treated animals.

Figure 18:
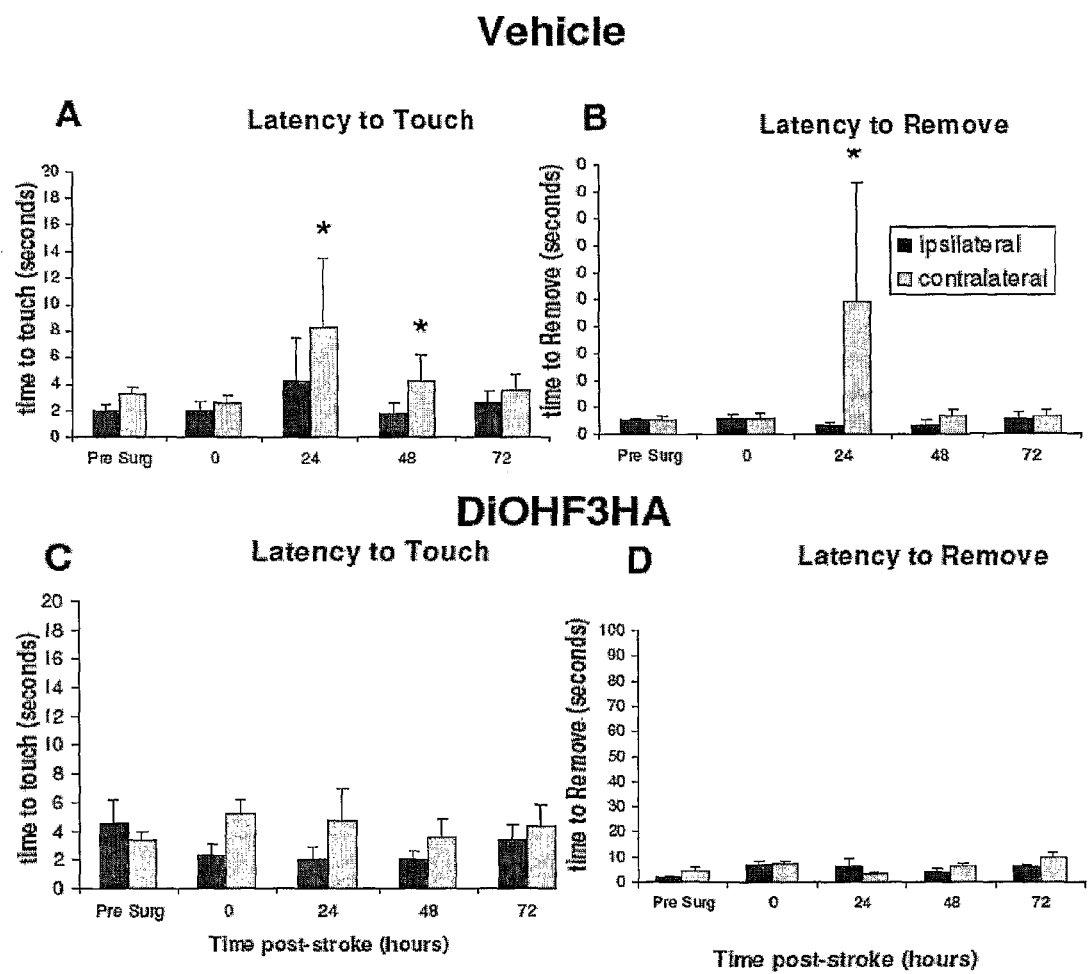

FIG. 18 illustrates the latency to touch (A & C) and remove (B & D) a stimulus on the contralateral forelimb compared with the ipsilateral forelimb assessed 24, 48, and 72 hours after ET-1-induced stroke and treatment with vehicle (A & B) or DiOHF3HA (15 mg/kg/day) (C & D) in mild to moderate stroke rats.

Figure 19:
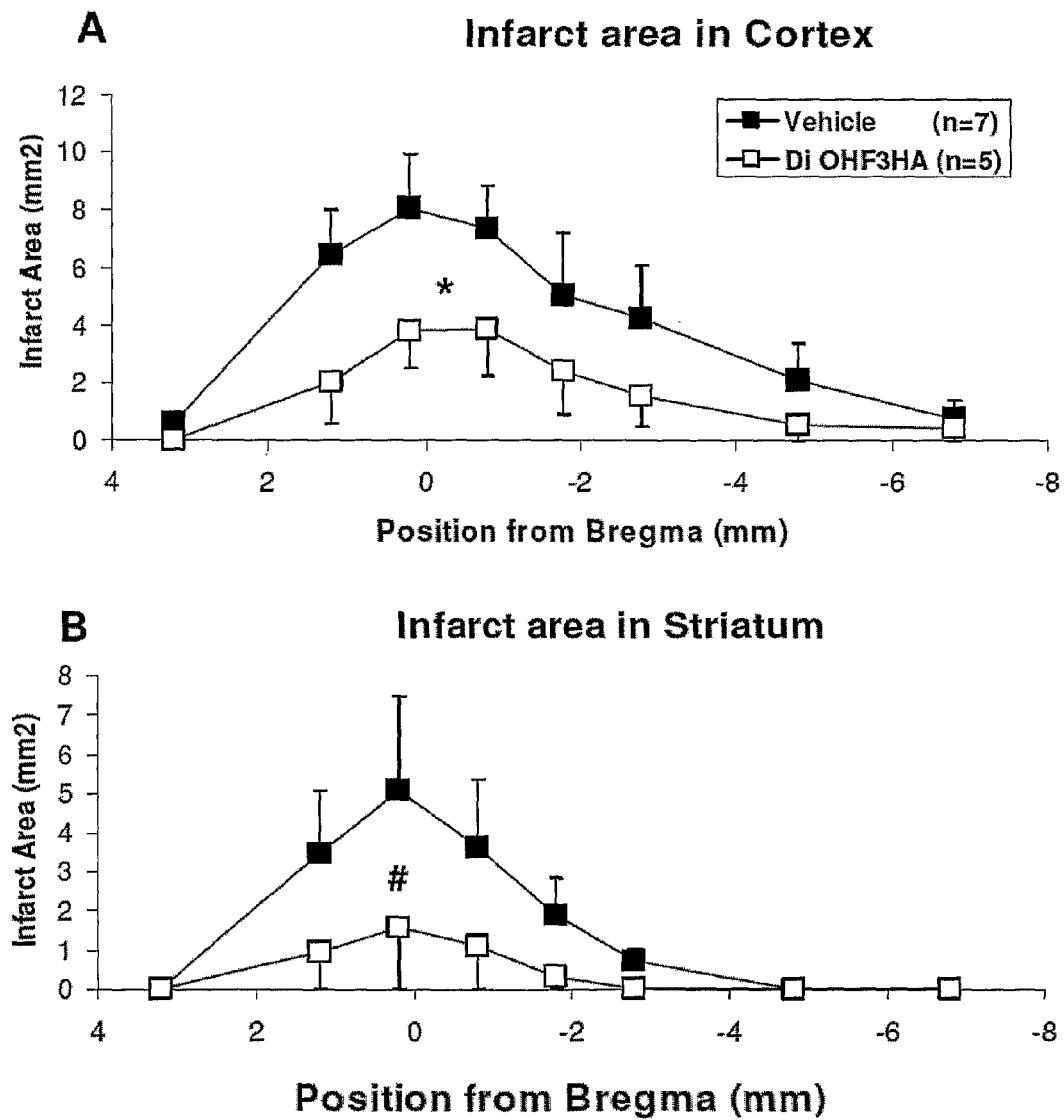

FIG. 19 illustrates the effect of delayed administration of DiOHF3HA (15 mg/kg/day) or vehicle on infarct area in cortex (A) and striatum (B) in mild to moderate stroke rats.

Definitions

As used herein, the term "alkyl" includes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be substituted or unsubstituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "lower" herein includes a linear or branched chain of 1 to 6 carbon atoms.

The term "alkylene" refers to a divalent alkyl as defined above, such as methylene (—$CH_2$—), propylene (—$CH_2CH_2CH_2$—), chloroethylene (—$CHClCH_2$—), 2-thiobutene —$CH_2CH(SH)CH_2CH_2$, 1-bromo-3-hydroxyl-4-methylpentene (—$CHBrCH_2CH(OH)CH(CH_3)CH_2$—), methylethylene, trimethylene, 1-propylene, 2-propylene, tetramethylene, 1-methyltrimethylene, 2-methyltrimethylene, 3-methyltrimethylene, 1-ethylethylene, 2-ethylethylene, pentamethylene, 1-methyltetramethylene, 2-methyltetramethylene, 3-methyltetramethylene, 4-methyltetramethylene and hexamethylene and the like.

The term "alkenyl" includes branched or unbranched hydrocarbon chains containing one or more carbon-carbon double bonds.

The term "alkynyl" includes branched or unbranched hydrocarbon chains containing one or more carbon-carbon triple bonds.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl naphthyl), which is optionally mono-, di-, or tri-substituted. The aryl groups herein are unsubstituted or, as specified, substituted in one or more substitutable positions with various groups.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_1$-$C_6$ alkenyl, $C_1$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1C_6$)alkylamino($C_1$-$C_6$)alkyl.

The term "acyl" includes an —C(O)R group, wherein R is alkyl or aryl as defined above, such as formyl, acetyl, propionyl, or butyryl.

The term "alkoxy" includes —OR—, wherein R is alkyl. The term "lower alkoxy radicals" there may be mentioned linear and branched alkoxy groups of 1 to 6 carbon atoms, such as methoxy, ethoxy, propoxy, isopropoxy, butoxy, isobutoxy, sec-butoxy, tert-butoxy, pentyloxy, isopentyloxy, hexyloxy and isohexyloxy groups.

The term "amido" includes an amide linkage: —C(O) NR— (wherein R is hydrogen or alkyl).

The term "amino" indicates an amine linkage: —NR—, wherein R is hydrogen or alkyl.

The term "carboxyl" indicates —C(O)O—, and the term "carbonyl" indicates —C(O)—.

The term "carbonate" indicates —OC(O)O—.
The term "sulfonate" indicates —$S(O)_2O^-$
The term "phosphonate ester" indicates
The term "carboxylic acid" indicates —C(O)OH.
The term "sulfonic acid" indicates —$S(O)_2OH$.
The term "phosphonic acid" indicates —$P(O)(OH)_2$.
The term "phosphamate" indicates —Ar—$NHPO_4^-$.
The term "phosphate ester" indicates —O—$P(O)(OR)_2$.
The term "sulfamate" indicates —Ar—$NHSO_3^-$.
The term "sulfonic esters" indicates —$S(O)_2$—OR.
The term "sulfonate" indicates —$S(O)_2O^-$.
The term "phosphonate ester" indicates R—$P(O)(OR)_2$.
The term "carboxylic acid" indicates —C(O)OH.
The term "sulfonic acid" indicates —$S(O)_2OH$.
The term "phosphonic acid" indicates —$P(O)(OH)_2$.
The term "phosphamate" indicates —Ar—$NHPO_4$.
The term "carbamate" indicates —NHC(O)O—.

The hydrocarbon chains can be optionally interrupted by one or more heteroatoms.

When present, the linker group may be any of a number of such molecules known in the area described herein.

As is clear from the above description, the spacer group D may be absent. It is also clear from the above description that the linker group may be absent.

DESCRIPTION OF THE EMBODIMENTS

The present invention provides flavonoid derivatives and compositions containing flavonoid derivatives, and methods of using same.

The presence of reactive oxidative species (ROS) in living tissue has been shown to be associated with many disorders in animals. Reactive oxidative species can contain both nitrogen, and oxygen, or only oxygen atoms. Some examples of ROS molecules include singlet $O_2$, $H_2O_2$, free radicals such as OH$^-$, $O_2^{-'}$, NO', and ROO'. Many of these species are formed during normal metabolic activity, but their concentration levels can be elevated under conditions of oxidative stress associated with chronic inflammation, infections and other diseases.

Many ROS molecules are the result of naturally occurring processes such as oxygen metabolism and inflammatory processes. For example, when cells use oxygen to generate energy, free radicals are created as a consequence of ATP production by the mitochondria. Exercise can increase the levels of free radicals as can environmental stimuli such as ionizing radiation (from industry, sun exposure, cosmic rays, and medical X-rays), environmental toxins, altered atmospheric conditions (e.g. hypoxia and hyperoxia), ozone and nitrogen oxide (primarily from automobile exhaust, therapeutics). Lifestyle stressors such as cigarette smoking and excessive alcohol consumption are also known to affect levels of free radicals. Radical species may combine to form other more damaging Or toxic species such as peroxynitrite ONOO$^-$, a product of superoxide and nitric oxide radical reaction.

Another source of ROS species is some therapeutic agents, such as anti-cancer drugs. Anthracycline derivatives are highly useful anti-cancer agents in the treatment of neoplastic diseases such as acute leukemia, malignant lymphoma, etc. However, an undesirable feature of their administration can be oxidative damage to tissue, which can lead to cardiomyopathy and possible heart failure. The presence of the therapeutic agent can therefore cause the development of congestive heart failure (CHF). This feature of some therapeutic agents can limit their effectiveness and it would be useful to develop an appropriate co-administration regime.

Thus in one aspect of the present invention, there is provided a method of preventing and/or at least ameliorating damage to a subject caused by the administration of a therapeutic agent, the method comprising co-administering to a subject:
 i) a therapeutic agent; and
 ii) an effective amount of at least one compound in accordance with Formula I, Formula II, Formula III or Formula IV, wherein $R^1$, $R^2$, $R^3$, $R^4$, $R^5$, $R^6$, $R^7$, $R^8$, $R^8$, U, Q, W, X, Y, Z, n have the same meaning as above, or a pharmaceutically acceptable salt or solvates thereof.

In another aspect, the present invention provides a method of preventing and/or at least ameliorating UV damage to the skin of a subject, comprising administering a therapeutically effective amount of the composition of the invention. With this aspect, preferably the composition is formulated into a sunscreen. The composition may be topically applied to the skin. The composition may contain emollients and moisturisers.

In another aspect the present invention provides a method of preventing and/or reversing the effects of ageing, of reducing apparent wrinkling and or/or treating or preventing dry skin.

In another aspect, the present invention provides a method of treating a subject having a disease or disorder involving oxidative damage, comprising administering a therapeutically effective amount of the composition of the invention.

Preferably, the disease or disorder involving oxidative damage is selected from the group consisting of cancer, heart disease, neurological disorders, auto-immune disorders, ischaemia-reperfusion injury, diabetic complications, septic shock, hepatitis, atherosclerosis, Alzheimer's disease and complications arising from HIV or Hepatitis, including Hepatitis B.

In another aspect, the present invention provides a
In a particular embodiment, the subject is an animal. The animal may be selected from the group consisting of humans, non-human primates, cattle, horses, pigs, sheep, goats, dogs, cats, birds, chickens or other poultry, ducks, geese, pheasants, turkeys, quails, guinea pigs, rabbits, hamsters, rats and mice.

In some aspects of the invention, the one or more flavonoid derivatives are administered simultaneously, separately or sequentially with the one or more therapeutic agent(s).

When used in such a combination the one or more therapeutic agent(s) and the one or more flavonoid derivative(s) according to the present invention can be administered as separate agents at the same or different times or they can be formulated as a single composition comprising both compounds.

Free radicals react with key organic substrates in cells such as lipids, proteins, and DNA. Oxidation of these bio-molecules can damage them, disturbing normal functions and may contribute to a variety of disease states. It has been noted that certain organ systems are predisposed to greater levels of oxidative stress or nitrosative stress. Those organ systems most susceptible to damage are the pulmonary system (exposed to high levels of oxygen), the brain (exhibits intense metabolic activity yet has lower levels of endogenous antioxidants), the eye (constantly exposed to damaging UV light), circulatory system (victim to fluctuating oxygen and nitric oxide levels) and reproductive systems (at risk from the intense metabolic activity of sperm cells).

Examples of relevant acute disorders causing the production of ROS include ischaemia reperfusion, stroke, myocardial infarction or mechanical trauma, such as a crush injury or surgery. Some forms of surgery such as heart bypass or transplant surgery necessarily cause ischaemia and reperfusion of tissue. Typically one or more flavonoid derivatives according to the present invention are administered to the subject before and/or during surgery.

Chronic disorders may be chosen from the group including cancer, cerebrovascular disease, atherosclerosis, artery disease including coronary disease, peripheral vascular disease (including damage caused by diseases such as diabetes), hypertension, pulmonary hypertension, chronic obstructive airways disease, emphysema, neurological disorders, auto-immune disorders, diabetic complications, septic and hypovolemic shock, burns, hepatitis, and complications arising from hepatitis and HIV. Another chronic disorder may be chosen from the complications resulting from administration of hyperbaric or high oxygen tension atmospheres, often applied to assist breathing particularly in a premature infant human, including retinal or other eye damage. Subjects at risk of relevant chronic disorders may be diagnosed by analysis of symptoms, diagnostic testing, enzymatic markers, or by genetic testing to identify a genetic predisposition. Predisposition to certain acute disorders such as heart attack or stroke may also be identified by genetic testing and may prompt the prophylactic application of one or more flavonoid derivatives to the subject at risk. Drug-induced disorders due to ROS eg drug induced congestive heart disease.

If the disease or disorder is stroke or risk or stroke, the composition described above is preferably administered before the stroke occurs as a prophylactic to reduce the risk of stroke occurrence, or within twelve hours (preferably within four hours) of stroke occuance.

An example of an ROS involved pathological condition is ischaemia where a deficiency of blood flow to part of a body results in inadequate tissue perfusion with oxygen. Ischaemia causes tissue damage, the severity of the damage depending on the length of time the tissue is deprived of oxygen and whether adequate reperfusion of oxygen occurs after the ischaemic event.

At least one compound in accordance with the present invention may be administered via a number of different routes, for example, topically, orally, subcutaneous, intra-muscular, intra-arterially and/or intravenously.

Compound Synthesis

The present invention provides flavonoid compounds according to Formula I, II, III or IV, V and methods of synthesizing such compounds.

Derivatives of Flavonoids

Flavonoid phosphate derivatives are produced by a selective protection/deprotection synthetic strategy.

3-Hydroxyflavone-3-phosphate disodium salt (5)

Figure 1:
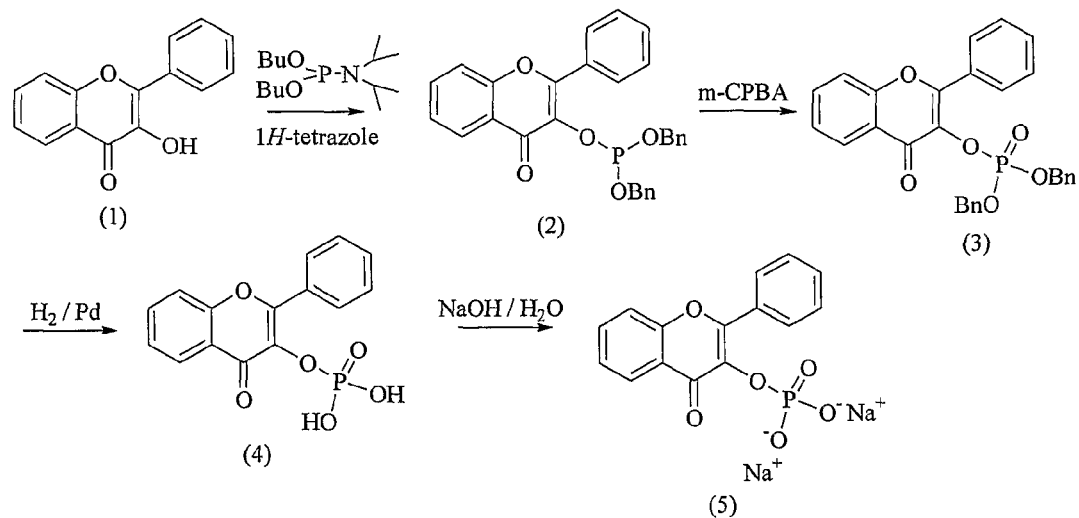
FIG. 1 illustrates the synthetic scheme for the synthesis of 3-hydroxyflavone-3-phosphate disodium salt (5).

With reference to FIG. 1 the approach to the synthesis of 3-hydroxyflavone-3-phosphate disodium salt is shown. 3-Hydroxyflavone (1) underwent phosphitylation when treated with dibenzyl N,N-diisopropylphosphoramidite and the intermediate phosphate was directly oxidised by m-chloroperbenzoic acid (mCPBA) to its corresponding protected phosphate. The phosphate ester was purified by flash chromatography followed by recrystallization, yield 45%.

The phosphate ester underwent hydrogenolysis in ethanol with palladium hydroxide to form the phosphate, which was immediately converted to its disodium salt by addition of a slight excess of 0.1 M sodium hydroxide solution. Deprotection by hydrogenolysis provided a pure sample of 3-hydroxyflavone-3-phosphate disodium salt in a 73% yield.

The corresponding diammonium salt was produced by ion exchange chromatography using a diethylaminoethyl column (DEAE) of (5).

3',4'-Dihydroxyflavone-3-phosphate (as disodium salt) (10)

Figure 2:
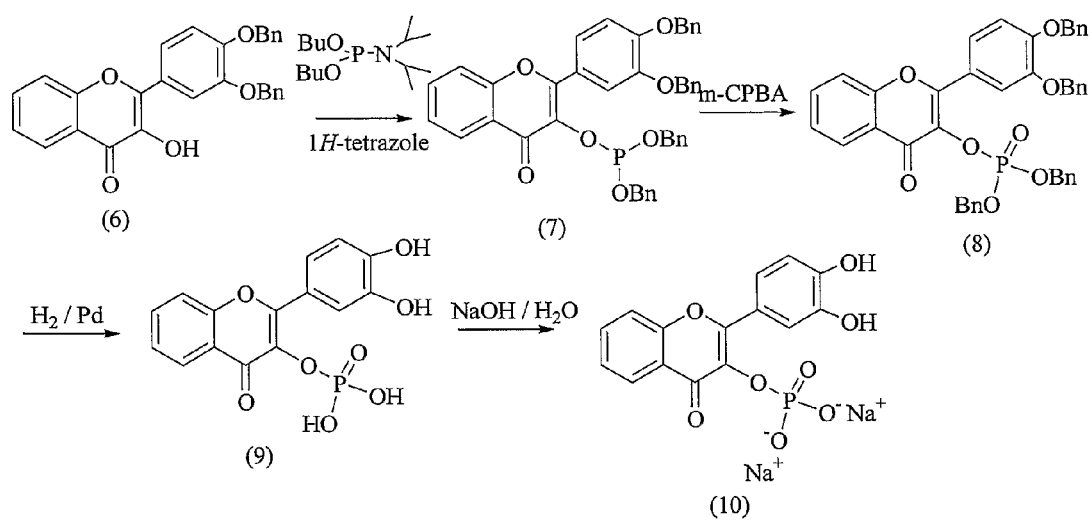
FIG. 2 illustrates the synthetic scheme for the synthesis of 3',4'-dihydroxyflavone-3-phosphate (10).

An identical procedure was implemented for the synthesis of the trihydroxyflavone analogue as shown in FIG. 2.

Thus 3',4'-dibenzyloxy-3-hydroxyflavone (6) underwent phosphitylation by diisopropyl N,N-dibenzyloxyphosphoramidite in the presence of 1H-tetrazole to form the 3',4'-dibenzyloxy-flavone-3-phosphite dibenzyloxy ester (7), which was oxidized by mCPBA to the protected phosphate ester, 3',4'-dibenzyloxy-flavone-3-phosphate dibenzyloxy ester (8). These two steps produced the desired compound in a 40% yield after recrystallisation.

The phosphate ester was then subjected to hydrogenolysis in ethanol with palladium to form the desired 3',3'-dihydroxyl-flavone-3-phosphate (9) which was converted to the corresponding disodium salt, 3',4'-dihydroxyl-flavone-3-phosphate disodium salt (10) by addition of NaOH.

Ester Derivatives of Flavonoids

3-Hydroxyflavone-3-hemisuccinate (15)

Figure 3:
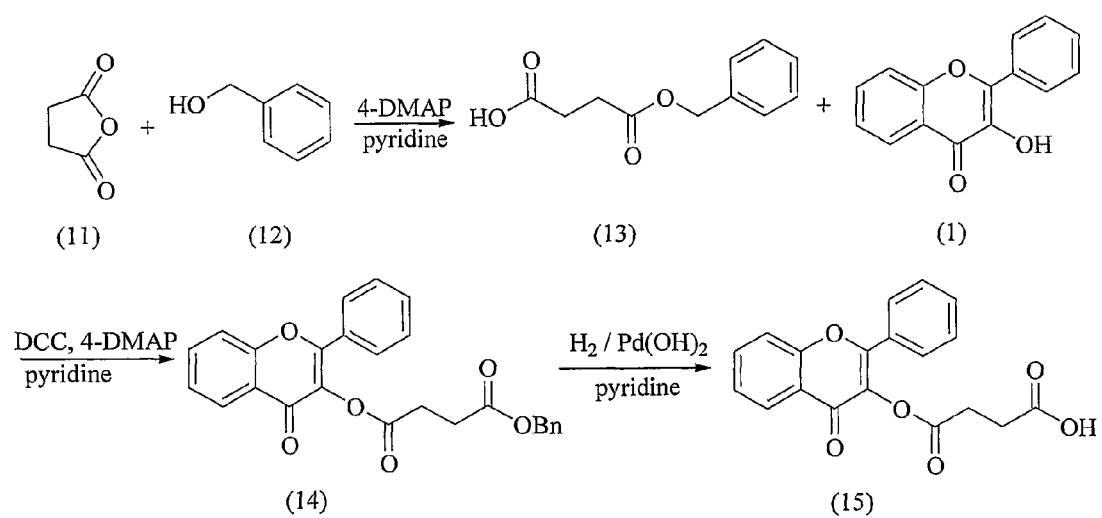
FIG. 3 illustrates the synthetic scheme for the synthesis of 3-hydroxyflavone-3-hemisuccinate (15) via the succinic acid monobenzyl ester.

3-Hydroxyflavone-3-hemisuccinate (15) was produced according to the reaction outlined in FIG. 3. Reaction of succinic anhydride (11) and benzyl alcohol (12) in the presence of 4-dimethylaminopyridine (DMAP) and pyridine in dichloromethane produced the succinic acid monobenzyl ester (13) as white crystalline flakes in 77% yield. This protected succinic acid derivative was coupled to 3-hydroxyflavone (1) in the presence of DCC and DMAP, forming flavone-3-hemisuccinate monobenzyl ester (14) as yellow or brown oil that solidified upon standing, with yields of up to 96% produced.

The deprotection of the monobenzyl ester to form the corresponding hemisuccinate using a Pd(OAc)$_2$ in the THF:EtOH:acetic acid solvent system, a larger scale reaction was undertaken to yield the required 3-hydroxyflavone-3-hemisuccinate (15).

3-Hydroxyflavone-3-hemiadipate (19)

Figure 4:
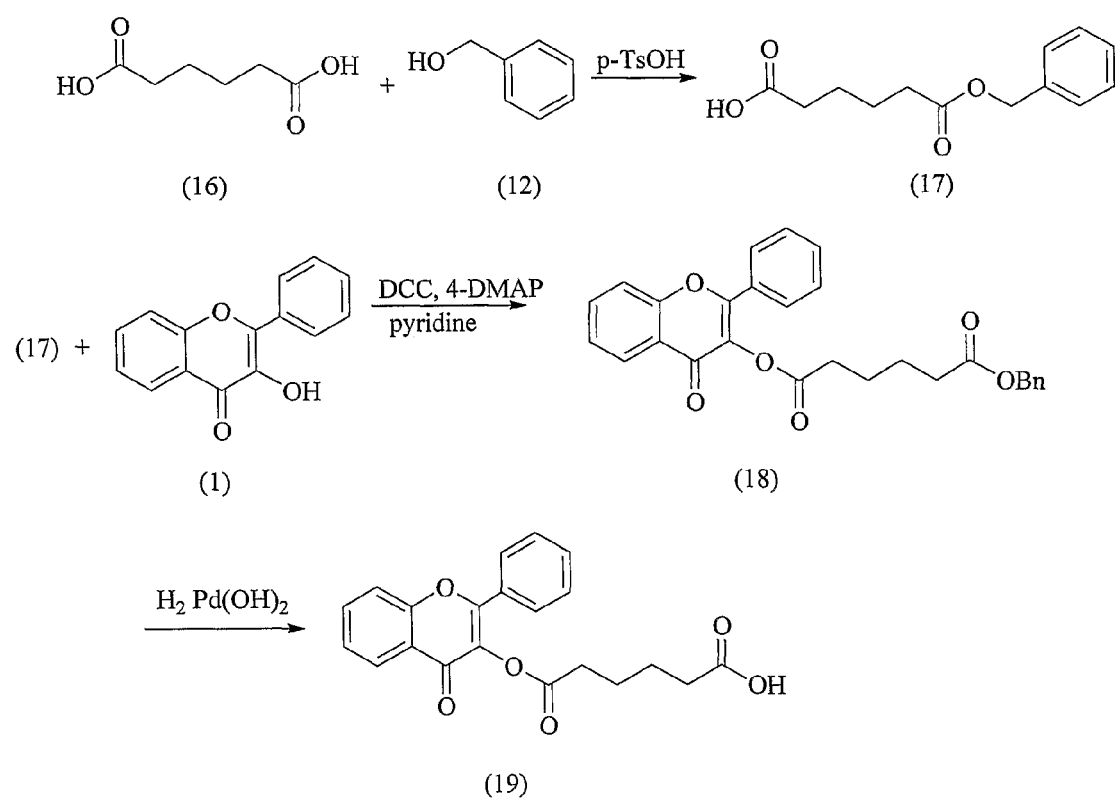
FIG. 4 illustrates the synthetic scheme for the synthesis of 3-hydroxyflavone-3-hemiadipate (19) via adipic acid monobenzyl ester.

3-Hydroxyflavone-3-hemiadipate (19) was synthesized following a similar procedure to that discussed above for the hemisuccinate, as shown in FIG. 4.

Adipic acid monobenzyl ester (17) was produced from adipic acid and benzyl alcohol in the presence of p-TsOH to yield the desired product as a colourless oil in 34% yield.

The protected adipic acid then underwent a DCC coupling with 3-hydroxyflavone (1) to form flavone-3-hemiadipate monobenzyl ester as a yellow/brown gum in 59% yield. Hydrogenation of this compound in the presence of Pd(OH)$_2$ catalyst, using a THF-based solvent system (9:1 THF:EtOH+ 0.05% acetic acid) resulted in hydrogenolysis of the monobenzyl ester, forming flavone-3-hemiadipate as a yellow solid in 89% yield.

3',4'-dihydroxyflavone-3-hemiadipate (21)

Figure 5:
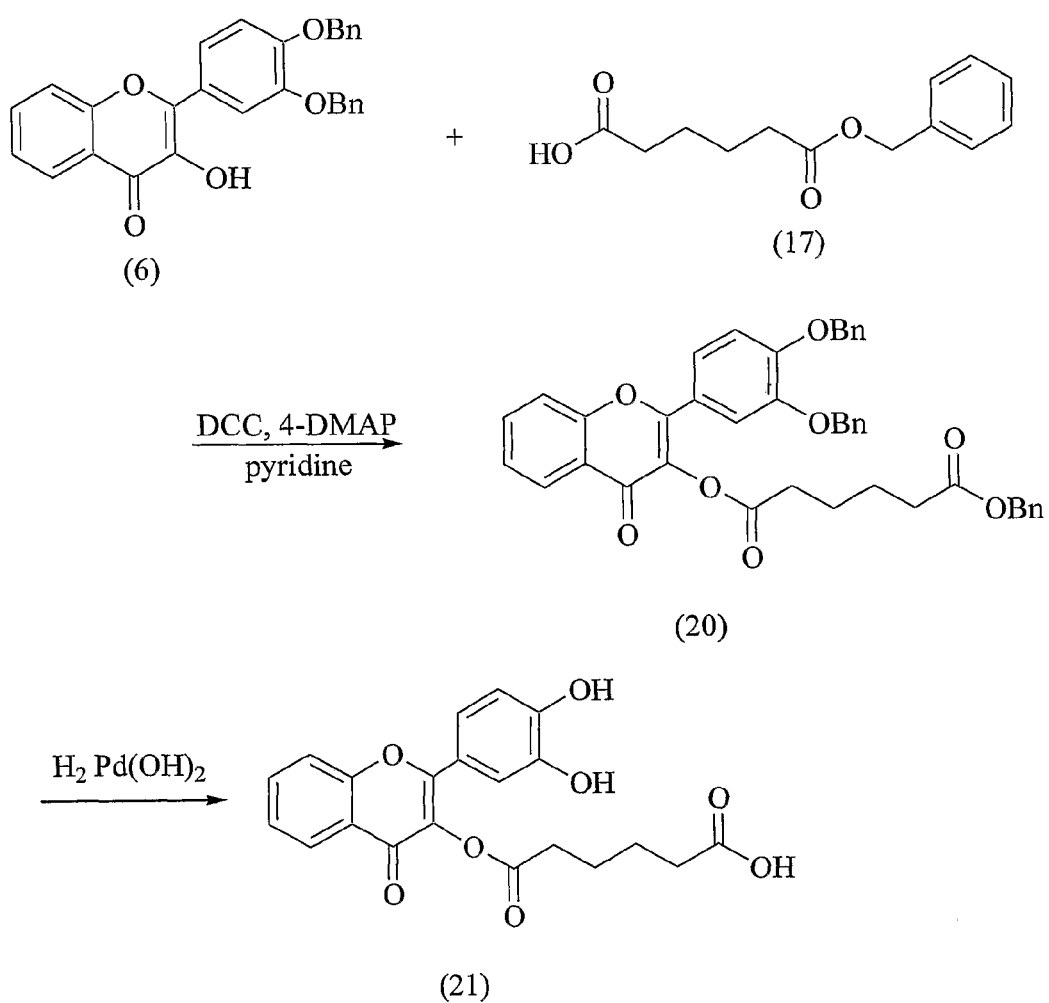
FIG. 5 illustrates tire synthetic scheme for the synthesis of 3',4'-dihydroxyflavone-3-hemiadipate (21).

The scheme for the synthesis of 3',4'-dihydroxyflavone-3-hemiadipate (21) is illustrated in FIG. 5. Following the methodology established above, 3',4'-dibenzyloxy-3-hydroxyflavone (6) and adipic acid monobenzyl ester (17) underwent a DCC coupling to produce the hemiadipate monobenzyl ester as a brown gum in 59% yield.

Deprotection by hydrogenolysis on a small scale (100-500 mg) proceeded smoothly to completion in 3-5 hours to give the 3',4'-dihydroxyflavone-3-hemiadipate (21) in 33% yield.

III Compositions and Methods

The compounds of this invention can be formulated in a variety of carriers and delivery systems. The amount of the therapeutic compound to be administered and the compound's concentration is dependent on the vehicle or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

Furthermore, excipients can be included in the formulation. Examples include co-solvents, surfactants, oils, humectants, emollients, preservatives, stabilizers and antioxidants. Any pharmacologically acceptable buffer may be used, e.g., Tris or phosphate buffers. Effective amounts of diluents, additives and excipients are those amounts which are effective to obtain a pharmaceutically acceptable formulation in terms of solubility, biological activity, etc.

Thus, a composition of the invention includes a therapeutic compound which can be formulated with conventional, pharmaceutically acceptable, vehicles for topical, oral or parenteral administration. Formulations can also include small amounts of adjuvants such as buffers and preservatives to maintain isotonicity, physiological and pH stability.

IV Administration

The compounds of the invention may be administered to both human and animal subjects.

The compounds of this invention may be administered in compositions wherein the active compound is intimately admixed with one or more inert ingredients and optionally including one or more additional active ingredients. The compounds may be used in any composition known to those skilled in the art for administration to humans and animals.

The composition of the invention may be administered through a proper route according to the dosage form. For example, the injection can be administered intravenous, intra-arterial, subcutaneous, intramuscular and the like.

For oral administration, either solid or fluid unit dosage forms can he prepared. The water soluble forms can be dissolved in an aqueous vehicle together with sugar, aromatic flavouring agents and preservatives to form syrup. An elixir is prepared by using a hydro-alcoholic (e.g., ethanol) vehicle with suitable sweeteners such as sugar and saccharin, together with an aromatic flavouring agent. Suspensions can be prepared with an aqueous vehicle with the aid of a suspending agent such as acacia, tragacanth, methylcellulose and the like. The synthetic flavonoid compounds of the present invention may also be formulated with stabilizing agents, for example metal chelator reducing agents such as ethylenediaminetetraacetic acid (EDTA) or a reducing agent such as sodium metabisufite.

Appropriate formulations for parenteral use are apparent to the practitioner of ordinary skill. Usually, the therapeutic compound is prepared in an aqueous solution in a concentration of from about 1 to about 100 mg/mL. More typically, the concentration is from about 10 to 60 mg/mL or about 20 mg/mL. Concentrations below 1 mg/mL may be necessary in some cases depending on the solubility and potency of the compound selected for use. The formulation, which is sterile, is suitable for various parenteral routes including intra-dermal, infra-articular, intramuscular, intravascular, intravenous, inhalation and subcutaneous.

Compositions according to the present invention may be formulated into sunscreens, skin care compositions, emollient of moisturizers.

Slow or extended-release delivery systems, including any of a number of biopolymers (biological-based systems), systems employing-liposomes, and polymeric delivery systems, for example dendrimers, can be utilized with the compositions described herein to provide a continuous or long term source of therapeutic compound. Such slow release systems are applicable to formulations for topical, ophthalmic, oral, and parenteral use.

The synthetic flavonoid compound(s) of the present invention may also be formulated as a nutrapharmaceutical or a nutraceutical. For example, the synthetic flavonoid compound(s) may be formulated into a food, such as a cereal, beverages such as fruit juice, alcoholic drinks, bread, etc, for oral consumption.

V Vasorelaxant and Antioxidant Activity of Flavonoid Derivatives

The effects of vehicle, flavone-3-hemiadipate ($10^{-8}$ to $10^{-4}$ M) and DiOHF ($10^{-4}$ M) on the level of superoxide anions generated in rat aorta in the presence of NADPH were determined and expressed as a percentage of control. The presence of the flavone-3-hemiadipate appeared to have no effect on the superoxide production at any concentration.

Figure 6:
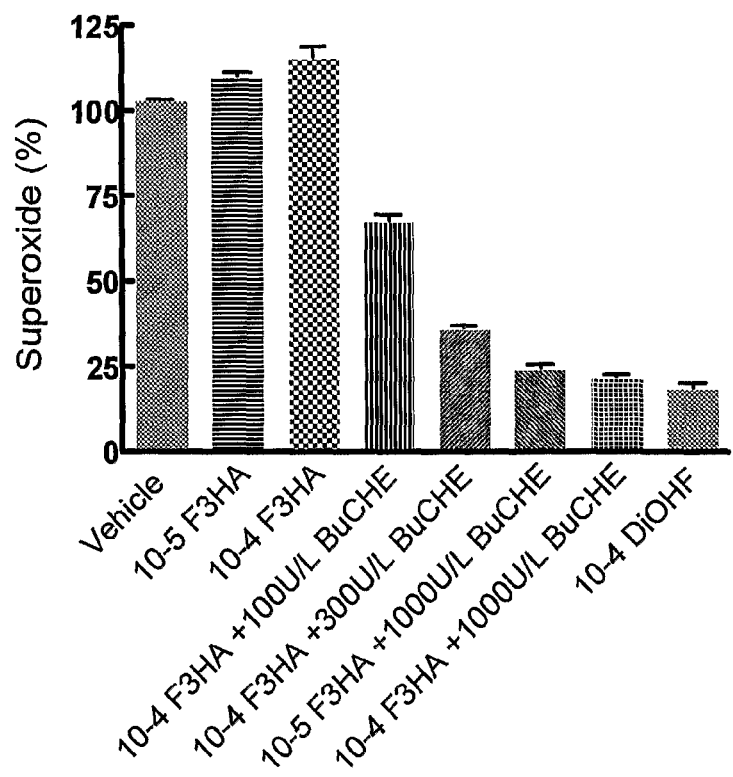
FIG. 6 illustrates the effects of vehicle ($dH_2O$), Flavone-3-hemiadipate (19) (F3HA), in the presence and absence of butyryl cholinesterase (BuCHE, 1000 U/L) and DiOHF ($10^{-4}$ M) on the level of superoxide anions generated in rat aorta in the presence of NADPH expressed as a percentage of control.

With reference to FIG. 6, the effects of vehicle, Flavone-3-hemiadipate (F3HA), in the presence and absence of butyryl cholinesterase (BuCHE, 1000 U/L) and DiOHF ($10^{-4}$ M) on the level of superoxide anions generated in rat aorta in the presence of NADPH expressed as a percentage of control is illustrated. In the absence of the esterase there appears to be no effect on the superoxide production. The presence of cholinesterase reveals a concentration-dependent inhibitory effect of flavone-3-hemiadipate. This is consistent with the hemiadipate group being removed in vitro to form the free hydroxyl derivative, 3-hydroxy flavone. The suppression of superoxide production by inclusion of both the flavone-3-hemiadipate (19) and esterase compares favourably to the activity of DiOHF (3',4'-dihydroxy flavonol). A reduction in the superoxide and other ROS concentrations has been linked to a possible reduction in myocardial damage induced by the presence of these radicals.

The concentration response curves to $Ca^{2+}$ in the presence of vehicle or increasing concentrations of flavone-3-hemiadipate (15) (F3HA, $10^{-8}$ M-$10^{-4}$ M) in endothelium intact aortic rings isolated from rats was determined. At the lower concentrations ($10^{-8}$ to $10-5$ M), the flavone-3-hemiadipate did not effect $Ca^{2+}$ contraction of the aortic ring. At the higher level tested, $10^{-4}$ M, the flavone-3-hemiadipate has some inhibitory effect, most likely due to the presence of an esterase in the aortic tissue of the rat.

The effects of vehicle (dH$_2$O), 3',4'-dihydroxyflavone-3-hemiadipate (21) (DiOHF3HA, $10^{-8}$ M-$10^{-4}$ M) and DiOHF ($10^{-4}$ M) on the level of superoxide anions generated in rat aorta in the presence of NADPH expressed as a percentage of control. The superoxide concentration remained constant throughout the DiOHF3HA concentration range studied, thus DiOHF3HA had no effect on superoxide generation.

Figure 7:
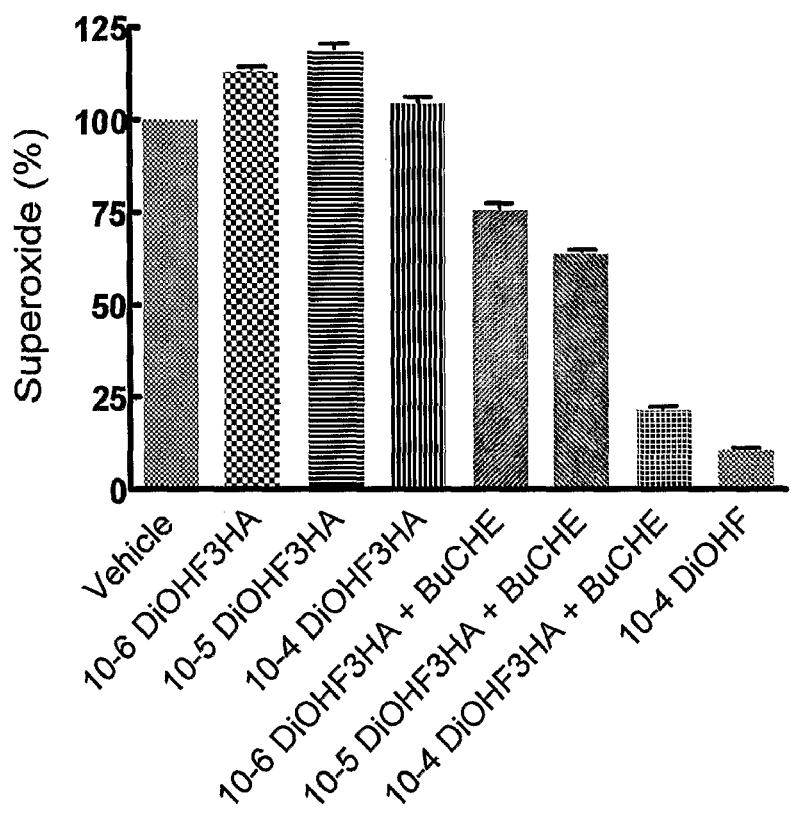
FIG. 7 illustrates the effects of Vehicle ($dH_2O$), 3',4'-dihydroxyflavone-3-hemiadipate (21) (DiOHF3HA, $10^{-6}$ M-$10^{-4}$ M) in the presence and absence of butyryl cholinesterase (BuCHE, 1000 U/L) and DiOHF ($10^{-4}$ M) on the level of superoxide anions generated in rat aorta in the presence of NADPH expressed as a percentage of control.

Referring to FIG. 7, the effects of vehicle, 3',4'-dihydroxyflavone-3-hemiadipate (21) (DiOHF3HA, $10^{-6}$ M-$10^{-4}$ M) in the presence and absence of butyryl cholinesterase (BuCHE, 1000 U/L) on the level of superoxide anions generated in rat aorta in the presence of NADPH expressed as a percentage of control is illustrated. For comparison the results using DiOHF ($10^{-4}$ M) on the level of superoxide anions generated in rat aorta in the presence of NADPH expressed as a percentage of control are also shown. The presence of the cholinesterase revealed a concentration dependent inhibition of superoxide levels.

The concentration response curves to $Ca^{2+}$ in the presence of vehicle or increasing concentrations of 3',4'-dihydroxyflavone-3-hemiadipate (21) (DiOHF3HA, $10^{-6}$ M-$10^{-4}$ M) in endothelium intact aortic rings isolated from rats. The contractions are expressed as a percentage of the initial response to $Ca^{2+}$ ($3\times10^{-3}$ M) observed before treatment with DiOHF3HA. DiOHF3HA appears to have slight Ca2+ inhibitory action at $10^{-4}$ M. This effect is possibly due to the presence of some esterase in the aortic tissue of the rat.

Figure 8:
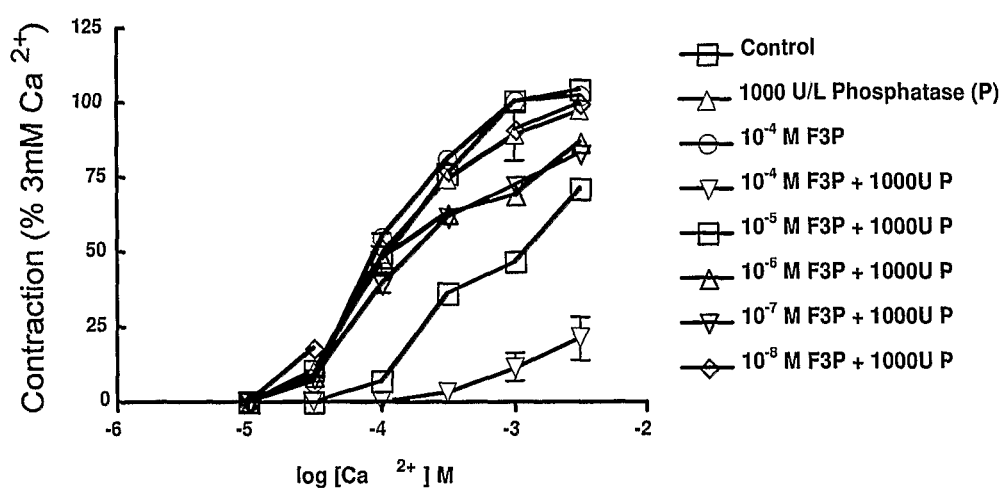
FIG. 8 illustrates the concentration response curves to $Ca^{2+}$ in the presence of vehicle or 3',4'-dihydroxyflavone-3-hemiadipate (21) (DiOHF3HA, $10^{-4}$ M), in the presence and absence of BuCHE, compared to DiOHF in endothelium intact aortic rings isolated from rats. The contractions are expressed as a percentage of the initial response to $Ca^{2+}$ ($3\times10^{-3}$ M) observed before treatment with DiOHF3HA.

Turning to FIG. 8, the concentration response curves to $Ca^{2+}$ in the presence of vehicle or 3',4'-dihydroxyflavone-3-hemiadipate (21) (DiOHF3HA, $10^{-4}$ M), in the presence and absence of BuCHE was compared to DiOHF in endothelium intact aortic rings isolated from rats is illustrated. The contractions are expressed as a percentage of the initial response to $Ca^{2+}$ ($3\times10^{-3}$ M) observed before treatment with DiOHF3HA. The presence of cholinesterase markedly enhanced the inhibitory effect of DiOHF3HA.

Figure 9:
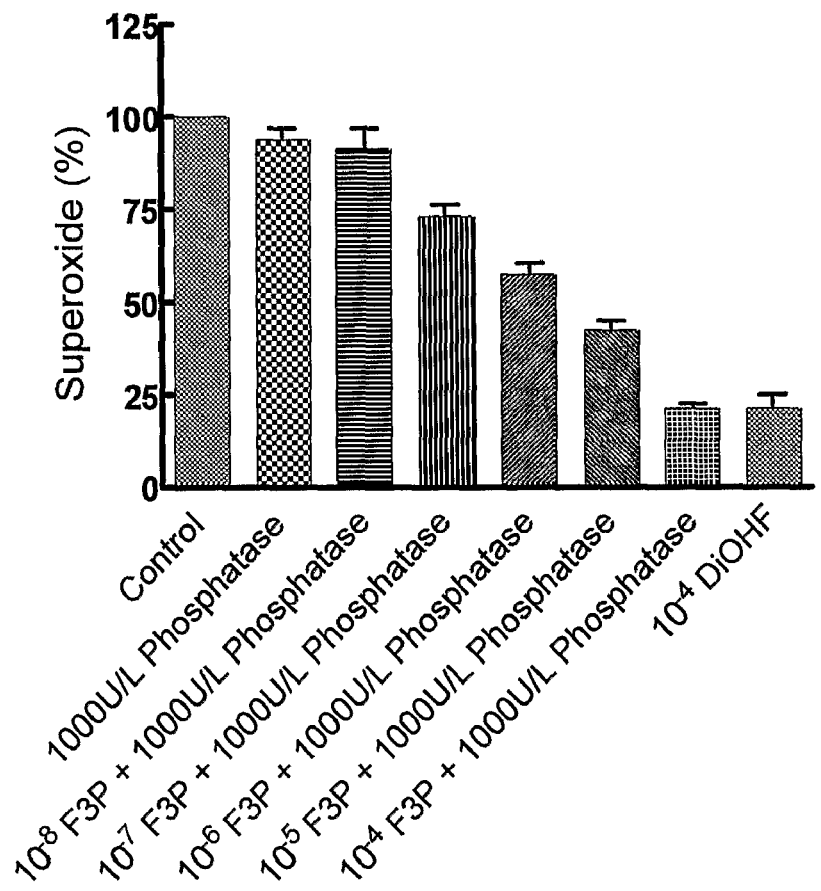
FIG. 9 illustrates the effects of vehicle ($dH_2O$), Flavone-3-phosphate (F3P, $10^{-8}$ M to $10^{-4}$ M) in the presence phosphatase (1000 U/L) and DiOHF ($10^{-4}$ M) on the level of superoxide anions generated in rat aorta in the presence of NADPH expressed as a percentage of control.

Referring to FIG. 9, the effects of vehicle, flavone-3-phosphate (F3P, $10^{-8}$ M-$10^{-4}$ M) in the presence phosphatase (1000 U/L) and DiOHF ($10^{-4}$ M) on the level of superoxide anions generated in rat aorta in the presence of NADPH expressed as a percentage of control. The presence of the flavone-3-phosphate caused a concentration dependent decrease in the levels of superoxide. This effect is contrary to previous studies that have shown that the presence of the 3',4'-dihydroxyl group in the B ring is determinative in decreasing the levels of superoxide.

The concentration response curves to $Ca^{2+}$ in the presence of vehicle or increasing concentrations of flavone-3-phosphate (F3P, $10^{-6}$ M-$10^{-4}$ M) in endothelium intact aortic rings isolated from rats was determined. Flavone-3-phosphate caused partial inhibition of the calcium-induced contraction at the highest concentration.

Figure 10:
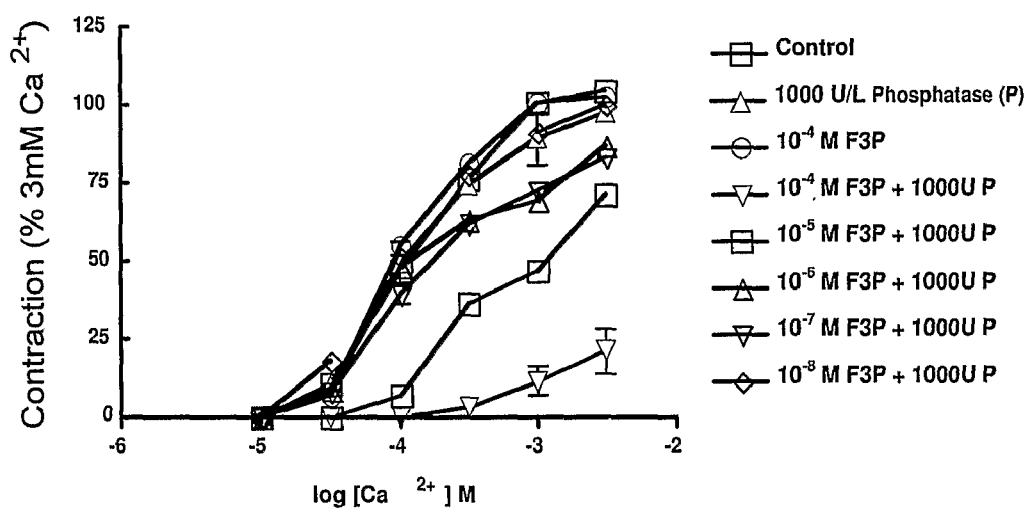
FIG. 10 illustrates the concentration response curves to $Ca^{2+}$ in the presence of vehicle or flavone-3-phosphate (F3P, $10^{-8}$ M to $10^{-4}$ M) in the presence and absence of phosphatase (P, 1000 U/L) in endothelium intact aortic rings isolated from rats. The contractions are expressed as a percentage of the initial response to $Ca^{2+}$ ($3\times10^{-3}$ M) observed before treatment with flavone-3-phosphate.

Referring to FIG. 10, the concentration response curves to $Ca^{2+}$ in the presence of vehicle or flavone-3-phosphate (F3P, $10^{-8}$ M-$10^{-4}$ M) in the presence and absence of phosphatase (P, 1000 U/L) in endothelium intact aortic rings isolated from rats is shown. The contractions are expressed as a percentage of the initial response to $Ca^{2+}$ ($3\times10^{-3}$ M) observed before treatment with flavone-3-phosphate. The presence of phosphatase markedly enhanced the inhibitory effects of flavone-3-phosphate. The invention is illustrated by the following non-limiting examples.

Synthesis of Flavonoid Derivatives 3-(Benzyloxycarbonylbutylcarbonyloxy)flavone

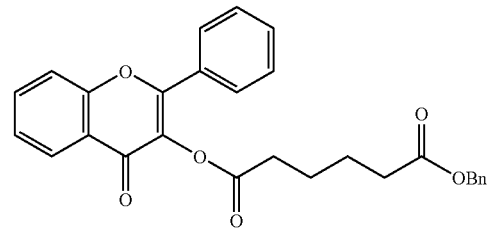

3-Hydroxyflavone (0.105 g, 0.442 mmol), dicyclohexylcarbodiimide (0.193 g, 0.933 mmol) and 4-dimethylaminopyridine (9.80 mg, 0.0802 mmol) was added to a solution of adipic acid monobenzyl ester (0.168 g, 0.754 mmol) in dichloromethane (10 mL) and the mixture was stirred under N$_2$ at room temperature for 19 h. Water (50 μL) was added and the resultant mixture was stirred for 10 min, then diethyl ether (10 mL) was added. The mixture was filtered, the filtrate concentrated and purified by flash chromatography (15-40%

EtOAc in toluene) to yield the monobenzyl ester as a yellow gum (0.16 g, 80%). A small portion was recrystallized from EtOAc/petroleum spirits to give a colourless powder; mp=74-76° C.; $^1$H NMR (399.7 MHz, CDCl$_3$) δ 1.60-1.75 (m, 4H, CO$_2$CH$_2$CH$_2$); 2.31 (t, J=6.8 Hz, 2H, CO$_2$CH$_2$); 2.55 (t, J=6.8 Hz, 2H, CO$_2$CH$_2$); 5.02 (s, 2H, CH$_2$Ph); 7.20-7.28, 7.39-7.45 (2m, H, PhCH$_2$, H3', 4', 5'); 7.34 (dd, 1H, $J_{5,6}$=8.0 Hz, $J_{6,7}$=7.6 Hz, H6); 7.46 (d, 1H, $J_{7,8}$=8.0 Hz, H8); 7.62 (ddd, 1H, $J_{5,7}$=1.6 Hz, $J_{6,7}$=7.6 Hz, $J_{7,8}$=8.0 Hz, H7); 7.73-7.77 (m, 2H, H2', 6'); 8.16 (dd, 1H, $J_{5,7}$=1.6 Hz, H5). $^{13}$C NMR (100.5 MHz, CDCl$_3$) δ 25.29 (2C, CO$_2$CH$_2$CH$_2$); 34.62, 34.91 (2C, CO$_2$CH$_2$); 67.30 (1C, CH$_2$Ph); 119,21, 124.68, 126.29, 127.17, 129.29, 129.40, 129.63, 129.75, 131.05, 132.36, 134.72, 135.06, 137.03, 156.71, 157.45 (20C, Ar); 171.54, 173.27, 174.16 (3C, C=O). Anal. Found: C, 73.54; H, 5.27; C$_{42}$H$_{36}$O$_8$ requires C, 73.67; H, 5.30%. HRMS (ESI$^+$) m/z 479.1469, C$_{28}$H$_{24}$NaO$_6$ [M+Na]$^+$ requires 479.1471.

3-Hydroxyflavone 3-hemiadipate

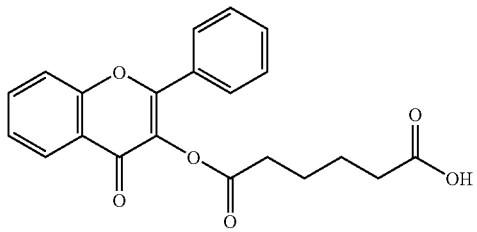

A mixture of 3-(benzyloxycarbonylbutylcarbonyloxy)flavone (312 mg, 0.7 mmol) and Pd(OH)$_2$ (49.4 mg) in 9:1 THF:EtOH+0.05% acetic acid (15 mL) was treated with H$_2$ for 5 h. The crude product was filtered (Celite), the filtrate was concentrated and the residue was purified by flash chromatography (10-25% EtOAc in toluene+1% acetic acid) to give the hemiadipate as a light yellow solid (0.211 g, 89%). A small portion was crystallized from EtOAc/petroleum spirits, mp=118-121° C.; $^1$H NMR (399.7 MHz, CDCl$_3$) δ 1.66-1.83 (m, 4H, CH$_2$CH$_2$CO$_2$); 2.38 (t, J=6.8 Hz, 2H, CH$_2$CO$_2$); 2.63 (t, J=6.8 Hz, 2H, CH$_2$CO$_2$); 7.42 (dd, 1H, $J_{5,6}$=8.0 Hz, $J_{6,7}$=8.0 Hz, H6); 7.47-7.53 (m, 3H, H3',4', 5'); 7.54 (d, 1H, $J_{7,8}$=8.4 Hz, H8); 7.70 (ddd, 1H, $J_{5,7}$=1.6 Hz, $J_{6,7}$=8.0 Hz, $J_{7,8}$=8.4 Hz, H7); 7.81-7.86 (m, 2H, H2', 6'); 8.24 (dd, 1H, $J_{5,6}$=8.0 Hz, $J_{5,7}$=1.6 Hz, H5). $^{13}$C NMR (100.5 MHz, CDCl$_3$) δ 25.01, 25.20 (2C, CO$_2$CH$_2$CH$_2$); 34.57 (2C, CO$_2$CH$_2$); 119.20, 124.66, 126.33, 127.21, 129.41, 129.76, 131.04, 132.40, 134.70, 135.10, 156.74, 157.60 (14C, Ar); 171.52, 173.38, 179.36 (3C, C=O). Anal. Found: C, 68.89; H, 4.91; C$_{21}$H$_{18}$O$_6$ requires C, 68.85; H, 4.95%. HRMS (ESI$^+$) m/z 389.1000, C$_{21}$H$_{18}$NaO$_6$ [M+Na]$^+$ requires 389.1001].

4'-(Benzyloxy)-3-(benzyloxycarbonylbutylcarbonyloxy)flavone

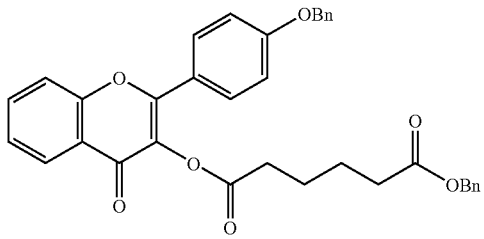

Ethylene dichloride (EDC) (843 mg, 4.40 mmol) was added to a solution of 4'-benzyloxy-3-hydroxyflavone (1.00 g, 2.90 mmol), adipic acid monobenzyl ester (1.30 g, 5.50 mmol) and DMAP (354 mg, 2.89 mmol) in dichloromethane (110 mL) and the mixture was stirred at rt overnight. The reaction mixture was then concentrated and the residue dissolved in ethyl acetate. The organic phase was washed with water (×3), 1 M HCl (×3), sat NaHCO$_3$ (×3), brine (×3), dried (MgSO$_4$) and concentrated. The residue was purified by flash chromatography (50% EtOAc/petrol) to give the benzyl ester as a brown oil, which was crystallized from EtOAc/petrol to give a colourless solid (900 mg, 55%); mp 93° C.; $^1$H NMR (500 MHz, CDCl$_3$) δ 1.77-1.83 (m, 4H, CH$_2$CH$_{b\ 2}$), 2.42 (t, 2H, J=7.5 Hz, CH$_2$CO), 2.67 (t, 2H, J=6.5 Hz, CH$_2$CO), 5.13 (s, 2H, CH$_2$Ph), 5.15 (s, 2H, CH$_2$Ph), 7.09 (d, 1H, $J_{7,8}$=8.5 Hz, H8), 7.35 (app. d, 2H, J=8.5 Hz, H2',6'), 7.40-7.46 (m, 11H, 2×Ph, H6), 7.69 (ddd, 1H, $J_{5,7}$=1.5, $J_{6,7}$=7.0, $J_{7,8}$=8.5 Hz, H7), 7.85 (app. d, 2H, J=8.5 Hz, H3',5'), 8.25 (d, 1H, $J_{5,6}$=8 Hz, H5); $^{13}$C NMR (125 MHz, CDCl$_3$) δ24.2 (×2), 33.6, 33.8 (4C, CH$_2$), 66.2, 70.1 (2C, CH$_2$Ph), 115.0, 117.9, 122.4, 123.5, 125.0, 126.0, 127.4, 128.1, 128.2, 128.5, 128.7, 130.0, 133.0, 133.7, 135.9, 136.2, 155.5, 156.1, 161.1 (Ar), 170.4, 172.0, 173.0 (3C, C=O); IR (thin film) 2937, 1760, 1730, 1646, 1602, 1507, 1468, 899 cm$^{-1}$; Anal. Found C, 74.67; H, 5.29, C$_{35}$H$_{30}$O$_7$ requires C, 74.72; H, 5.37%.

4'-Hydroxyflavone 3-hemiadipate

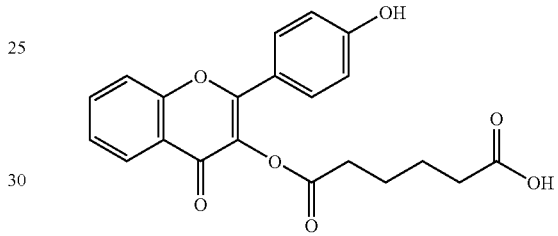

A mixture of the 4'-(benzyloxy)-3-(benzyloxycarbonyl butylcarbonyloxy) flavone (400 mg, 0.711 mmol) and Pd(OH)$_2$ (56 mg) in THF (10 mL), ethanol (1.2 mL) and AcOH (100 µL) was treated with hydrogen (50 psi) for 18 h. The reaction mixture was then filtered (Celite) and the pad washed with THF. The filtrate was concentrated and the solid residue was purified by flash chromatography (70% THF/toluene+1% AcOH) and the resultant solid recrystallised from THF/petrol to afford the acid as a colourless solid (150 mg, 55%); mp 177-180° C.; $^1$H NMR (500 MHz, d$_6$-DMSO) δ 1.56-1.66 (m, 4H, CH$_2$CH$_2$), 2.25 (t, 2H, J=7.0 Hz, CH$_2$CO), 2.64 (t, 2H, J=7.0 Hz, CH$_2$CO), 6.96 (app. d, 2H, J=8.5 Hz, H2',6'), 7.52 (t, 1H, $J_{6,7}$=$J_{7,8}$=7.5 Hz, H7), 7.80 (app. d, 2H, J=7.5 Hz, H3',5'), 7.78 (m, 1H, H8), 7.85 (t, 1H, $J_{5,6}$=$J_{6,7}$=7.5 Hz, H6), 8.06 (d, 1H, $J_{5,6}$=8.0 Hz, H5); $^{13}$C NMR (125 MHz, d$_6$-DMSO) δ 23.8, 23.9, 32.9, 33.3 (4C, CH$_2$), 115.9, 118.5, 119.7, 122.7, 125.0, 125.6, 130.1, 131.9, 134.5, 154.9, 155.8 160.6 (Ar), 170.4 170.9, 174.3 (3C, C=O); IR 3257, 2944, 2869, 1765, 1706, 1595, 854 cm$^{-1}$; HRMS (ESI$^+$) m/z 383.1123, C$_{21}$H$_{19}$O$_7$ [M+H]$^+$ requires 383.1131.

3',4'-Dibenzyloxy-3-(benzyloxycarbonylbutylcarbonyloxy) flavone

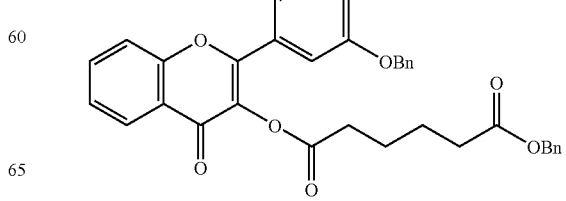

Adipic acid monobenzyl ester (1.91 g, 5.04 mmol) followed by EDC hydrochloride (0.764 g, 3.98 mmol) and DMAP (0.324 g, 2.65 mmol) were added to a stirring solution of 3',4'-dibenzyloxyflavonol (1.21 g, 2.68 mmol) in dry dichloromethane (100 mL) and the resultant mixture was stirred at room temperature under $N_2$ for 3 h. The reaction mixture was concentrated under reduced pressure and resuspended in ethyl acetate (100 mL). The suspension was then washed with water (3×50 mL), 1M HCl (3×50 mL), saturated $NaHCO_3$ (3×50 mL) and brine (3×50 mL). The organic extract was dried ($MgSO_4$), filtered, concentrated under reduced pressure and the yellow residue crystallized from EtOAc/petroleum spirits to yield the benzyl ester as a fluffy yellow solid (1.58 g, 88%); mp=84-85° C.; $^1$H NMR (399.8 MHz, $CDCl_3$); δ 1.70-1.80 (m, 4H, $CH_2CH_2$); 2.38 (t, 2H, J=6.8 Hz, $CH_2CO$); 2.55 (m, 2H, $CH_2CO$); 5.10 (s, 2H, $CH_2Ph$); 5:20 (s, 2H, $CH_2Ph$); 5.24 (s, 2H, $CH_2Ph$); 7.01 (d, 1H, $J_{7,8}$=8.4 Hz, H8); 7.26-7.49 (m, 19H, Ar, H6, 2', 5', 6'); 7.62 (ddd, 1H, $J_{5,7}$=1.2 Hz, $J_{6,7}$=7.2 Hz, $J_{7,8}$=8.4 Hz, H7); 8.22 (dd, 1H, $J_{5,6}$=7.6 Hz, $J_{5,7}$=1.2 Hz, H5). $^{13}$C NMR (100.5 MHz, $CDCl_3$) δ 25.33 (2C, $CH_2CH_2CO_2$); 34.59, 34.93 (2C, $CH_2CO_2$); 67.30, 71.91, 72.59 (2C, $CH_2Ph$); 114.77, 115.84, 119.06, 123.76, 123.84, 124.60, 126.19, 127.12, 128.25, 128.36, 129.15, 129.29, 129.64, 129.73, 130.12, 134.23, 134.89, 137.05, 137.54, 137.85, 149.61, 152.64, 156.53, 157.00 (32C, Ar); 171.49, 173.12, 174.18 3C, C=O). Anal. Found: C, 75.39; H, 5.47; $C_{42}H_{35}O_8$ requires C, 75.43; H, 5.43%. HRMS ($ESI^+$) m/z 691.2303, $C_{42}H_{36}NaO_8$ [M+Na]+ requires 691.2308.

3',4'-Dihydroxyflavone 3-hemiadipate

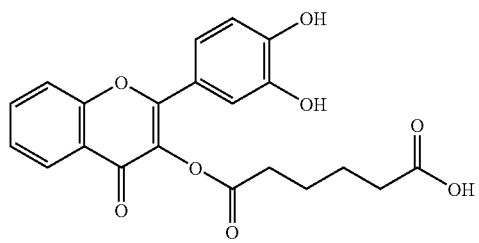

A mixture of 3',4'-dibenzyloxy-3-(benzyloxycarbonylbutylcarbonyloxy)flavone (2.12 g, 3.16 mmol) and $Pd(OH)_2$ (107 mg) in 9:1 THF:EtOH containing 0.05% acetic acid (50.0 mL) was treated with $H_2$ under high pressure for 5 h. The reaction mixture was filtered (Celite) and concentrated to give a dark green solid. The green residue was purified by flash chromatography (30-90% THF/toluene+1% acetic acid) followed by crystallization from THF/petroleum spirits to yield the pure hemiadipate as a pale brown solid (0.70 g, 56%); mp=194-197° C.; $^1$H NMR (399.8 MHz, $CDCl_3$); δ 1.44-1.62 (m, 4H, $CH_2CH_2$); 2.10 (t, 2H, J=6.8 Hz, $CH_2CO$); 2.44 (t, 2H, J=6.8 Hz, $CH_2CO$); 6.73 (d, 1H, $J_{5',6'}$=8.4 Hz, H5'); 7.09 (dd, 1H, $J_{2',6'}$=2.0 Hz, $J_{5',6'}$=8.4 Hz, $H_6$'); 7.16-7.22 (m, 2H, H6, 2'); 732 (d, 1H, $J_{7,8}$=8.0 Hz, H8); 7.48 (ddd, 1H, $J_{5,7}$=1.6 Hz, $J_{6,7}$=6.8 Hz, $J_{7,8}$=8.0 Hz, H7); 7.94 (dd, 1H, $J_{5,6}$=8.4 Hz, $J_{5,7}$=1.6 Hz, H5). $^{13}$C NMR (100.5 MHz, $d_6$-DMSO) δ 25.30, 25.62 (2C, $CH_2CH_2CO_2$); 34.43, 34.81 (2C, $CH_2CO_2$); 116.59, 117.42, 119.98, 121.41, 122.06, 124.13, 126.51, 127.07, 133.32, 136.04, 146.97, 150.65, 156.35, 157.27 (14C, Ar); 171.97, 173.46, 179.95 (3C, C=O). Anal. Found; C, 68.89; H, 4.91; $C_{21}H_{18}O_6$ requires C, 68.85; H, 4.95%. HRMS ($ESI^+$) m/z 389.1000, $C_{21}H_{18}NaO_6$ [M+Na]+ requires 389.1001.

3.4'-Di-(benzyloxycarbonylbutylcarbonyloxy)flavone

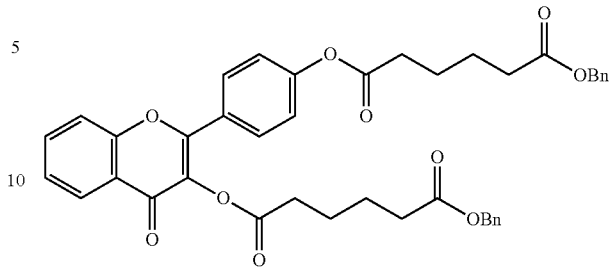

Ethylene dichloride (1.13 g, 5.91 mmol) was added to a solution of 3,4'-dihydroxyflavone (500 mg, 1.97 mmol), adipic acid monobenzyl ester (1.86 g, 7.88 mmol) and DMAP (481 mg, 3.94 mmol) in dichloromethane (30 mL) and the mixture stirred at rt for 50 min. The reaction mixture was then concentrated and the residue dissolved in ethyl acetate. The organic phase washed with water (×3), 1 M HCl (×3), sat $NaHCO_3$ (×3), brine (×3), dried ($MgSO_4$) and concentrated. The residue was purified by flash chromatography (50% EtOAc/petrol) to give the diester as a colourless oil, which was crystallized from EtOAc/petrol to afford a colourless solid (850 mg, 62%); mp 79° C.; $^1$H NMR (500 MHz, $CDCl_3$) δ 1.76-1.82 (m, 8H, 2×$CH_2CH_2$), 2.42 (t, 2H, J=7.0 Hz, $CH_2CO$), 2.45 (t, 2H, J=7.0 Hz, $CH_2CO$), 2.62 (t, 2H, J=7.0 Hz, $CH_2CO$), 2.65 (t, 2H, J=7.0 Hz, $CH_2CO$), 5.12 (s, 2H, $CH_2Ph$), 5.14 (s, 2H, $CH_2Ph$), 7.25 (d, 2H, J=8.5 Hz, H2',6'), 7.31-7.37 (m, 10H, 2×Ph), 7.44 (t, 1H, $J_{5,6}$=$J_{6,7}$=8.5 Hz, H6), 7.55 (d, 1H, $J_{7,8}$=8.5 Hz, H8), 7.72 (td, 1H, $J_{6,7}$=$J_{7,8}$=8.5, $J_{7,5}$=1.5 Hz,H7), 7.89 (d, 2H, J=8.5 Hz, H3',5'), 8.25 (dd, 1H, $J_{5,6}$=8.5$J_{5,7}$=1.5 Hz, H8); $^{13}$C NMR (125 MHz, $CDCl_3$) δ 24.16, 24.17, 24.21, 33.5, 33.8, 33.9, 66.1, 66.3 ($CH_2$), 118.0, 121.9, 123.5, 125.2, 126.1, 127.4, 128.1, 128.18, 128.22, 128.49, 128.53, 129.7, 133.7, 134.0, 135.9, 136.0, 152.8, 155.4, 155.5 (Ar), 170.3, 171.2, 172.1, 173.97, 173.0 (5C, C=O); IR 2943, 1765, 1732, 1652, 1501, 1465, 902 $cm^{-1}$; Anal. Found C, 71.30; H, 5.56, $C_{41}H_{38}O_{10}$ requires C, 71.29; H, 5.55%.

Flavone 3,4'-bis(hemiadipate)

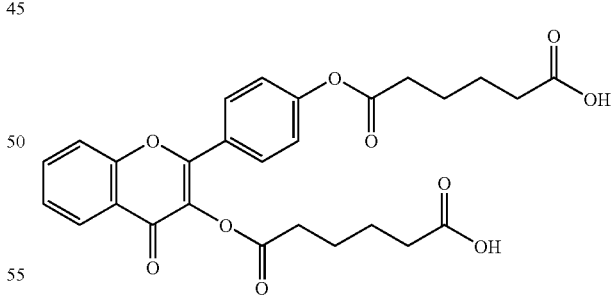

A mixture of 3,4'-di-(benzyloxycarbonylbutylcarbonyloxy)flavone (435 mg, 0.629 mmol) and $Pd(OH)_2$ (50 mg) in EtOAc (5 mL) was treated with hydrogen for 2 h resulting in a grey precipitate. THF was added to dissolve the precipitate and the mixture was filtered (Celite). The pad washed with THF, and the filtrate concentrated. The solid residue was recrystallised from THF/petrol to afford the bis(hemiadipate) as a colourless solid (183 mg, 50%); mp 133° C.; $^1$H NMR (500 MHz, $d_6$-DMSO) δ 1.55-1.70 (m, 8H, $CH_2CH_2$), 2.24 (t, 2H, J=7.0 Hz, $CH_2CO$), 2.27 (t, 2H, J=7.0 Hz, $CH_2CO$), 2.63

(t, 2H, J=7.0 Hz, CH$_2$CO), 2.64 (t, 2H, J=7.0 Hz, CH$_2$CO), 7.37 app. d, 2H, J=9.0 Hz, H3',5'), 7.55 (dd, 1H, J$_{5,6}$=8.5, J$_{6,7}$=7.5, Hz, H6), 7.80 (d, 1H, J$_{7,8}$=8.5 Hz, H8), 7.88 (ddd, 1H, J$_{6,7}$=7.5, J$_{7,8}$=8.5, J$_{5,7}$=1.5 Hz, H7), 7.96 (app. d, 2H, J=9.0 Hz, H2',6'), 8.08 (dd, 1H, J$_{5,6}$=8.5, J$_{5,7}$=1.5 Hz, H5); $^{13}$C NMR (125 MHz, d$_6$-DMS) δ 23.77, 23.82, 32.6, 33.2, 33.3; 44.3 (CH$_2$), 118.7, 122.5, 122.6, 122.7, 125.1, 126.8, 129.7, 132.9, 134.8, 152.7, 154.9, 155.1 (Ar), 170.4, 171.1, 171.4, 174.3, 174.3 (5C, C=O); IR 3059, 2940, 2873, 1768, 1706, 1504, 759 cm$^{-1}$; HRMS (ESI$^-$) m/z 509.1441, C$_{27}$H$_{25}$O$_{10}$ [M–H]$^-$ requires 509.1442.

3,7-Di-(benzyloxycarbonylbutylcarbonyloxy)flavone

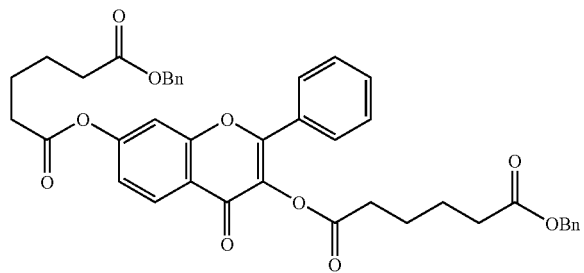

Ethylene dichloride (EDC) (517 mg, 2.7 mmol) was added to a solution of 3,7-dihydroxyflavone (250 mg, 0.983 mmol), adipic acid monobenzyl ester (921 mg, 3.90 mmol) and DMAP (220 mg, 1.80 mmol) in dichloromethane (25 mL) and the mixture was stirred at rt for 1 h. The reaction mixture was then concentrated and the residue dissolved in ethyl acetate. The organic phase was washed with water (×2), 1 M HCl (×2), sat NaHCO$_3$ (×2), brine (×2), dried (MgSO$_4$) and concentrated. The residue was filtered through a pad of silica eluting with 50% EtOAc/petrol to give a solid, which was recrystallized from EtOAc/petrol to give the diester as a colourless solid (565 mg, 91%); mp 58° C.; $^1$H NMR (500 MHz, CDCl$_3$) δ 1.74-1.82 (m, 8H, CH$_2$CH$_2$×2), 2.39 (t, 2H, J=7.0 Hz, CH$_2$CO), 2.45 (t, 2H, J=7.0 Hz, CH$_2$CO), 2.62-2.64 (m, 4H, CH$_2$CO×2), 7.15-7.17 (m, 2H, H2', 6'), 7.30-7.36 (m, 10H, 2×Ph), 7.39 (d, 1H, J$_{6,8}$=1.6 Hz, H8), 7.48-7.51 (m, 2H, H3', 5') 7.81-7.83 (m, 2H, 4' H6) 8.25 (d, 1H, J$_{5,6}$=9, H5); $^{13}$C NMR (125 MHz, CDCl$_3$) δ 24.1, 24.20, 24.21, 33.5, 33.80,3 3.82, 34.0, 44.7, 66.2, 66.3, (CH$_2$), 111.0, 119.5, 121.5, 172.5, 128.19, 128.22, 128.3, 128.5, 128.6, 128.7, 129.8, 131.3, 133.7, 135.9, 136.0, 154.8, 156.1, 156.6 (Ar), 170.3, 170.8, 171.5, 172.96, 173.0 (5C, C=O) IR 3071, 3035, 2944, 2876, 1760, 1726, 1615, 848 cm$^{-1}$; Anal. Found C, 71.34; H, 5.60%, C$_{41}$H$_{38}$O$_{10}$ requires C, 71.29; H, 5.55%.

3.7-Dihydroxyflavone 3,7-bis(hemiadipate)

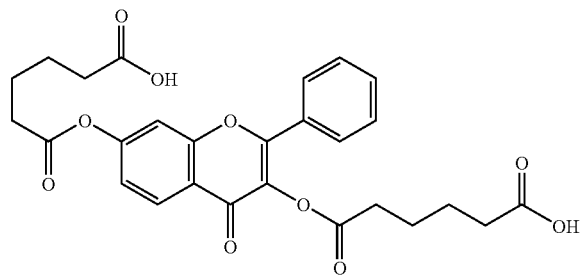

A mixture of 3,7-di-(benzyloxycarbonylbutylcarbonyloxy)flavone (565 mg, 0.818 mmol) and Pd(OH)$_2$ (65 mg) in EtOAc (10 mL) was treated with hydrogen for 3 h. A grey precipitate formed and THF was added until it dissolved. The mixture was filtered (Celite) and the pad washed with THF, and the filtrate was concentrated. The solid residue was recrystallised from THF/petrol to afford the diacid as a colourless solid (311 mg, 76%); mp 128° C.; $^1$H NMR (400 MHz, d$_6$-DMSO) δ 1.55-1.74 (m, 8H, CH$_2$CH$_2$×2), 2.23 (t, 2H, J=7.0 Hz, CH$_2$CO), 2.28 (t, 2H, J=7.0 Hz, CH$_2$CO), 261-2.68 (m, 4H, CH$_2$CO×2), 7.34 (m, 1H, H4'), 7.58-7.61 (m, 3H, H6, H2', 6'), 7.68 (d, 1H, J$_{6,8}$=1.6 Hz, H8). 7.87-7.89 (m, 2H, H3', 5'), 8.12 (d, 1H, J$_{5,6}$=8.8 Hz, H5); $^{13}$C NMR (100 MHz, d$_6$-DMSO) δ 23.7, 23.76, 23.78, 23.9, 32.9, 33.19, 33-24, 33.28 (CH$_2$), 111.9, 120.5, 120.6, 126.6, 128.1, 129.0, 129.2, 131.7, 133.0, 154.9, 155.6, 155.9 (Ar), 170.4, 170.6, 171.1, 174.2, 174.3 (5C, C=O); IR 3035, 2952, 2920, 1762, 1708, 1112 cm$^{-1}$; Anal. Found C, 63.64; H, 5.14%, C$_{27}$H$_{26}$O$_{10}$ requires C, 63,53; H, 5.13%.

Preparation of Flavonol Phosphates

3(Dibenzyloxyphosphoryloxy)flavone

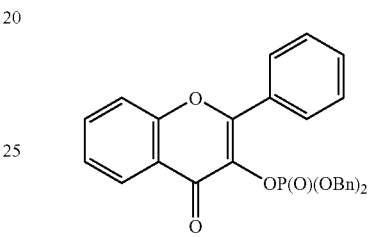

Dibenzyl diisopropylphosphoramidite (12.5 mL, 38.0 mmol) and 1H-tetrazole (74.0 mL, 31.7 mmol) was added to a solution of 3-hydroxyflavone (3.00 g, 12.6 mmol) in dry dichloromethane (150 mL). The reaction mixture was stirred under N$_2$ at room temperature for 2 h. The mixture was then cooled to −78° C. and m-CPBA (8.72 g, 50.6 mmol) was added. The mixture was allowed to return to room temperature and stirred for a further 45 min. The reaction mixture was washed with 0.25 M Na$_2$S$_2$O$_4$ (3×100 mL), saturated NaHCO$_3$ (3×100 mL) and water (2×100 mL). The organic extract was dried. (MgSO$_4$), filtered and concentrated under reduced pressure to yield a crude white solid. The crude material was purified by flash chromatography (20-50% EtOAc in toluene) followed by crystallization for EtOAc/ petroleum spirits to give the protected phosphate as a white fluffy solid (5.28 g, 84%); mp=85-88° C.; $^1$H NMR (399.7 MHz, CDCl$_3$); δ 5.09-5.17 (m, 4H, CH$_2$Ph); 7.22-7.30, 7.38-7.47 (2×m, 14H, Ar, H3', 4', 5', 6'); 7.51 (d, J$_{7,8}$=8.5 Hz, H8); 7.69 (ddd, J$_{5,7}$=1.5 Hz, J$_{6,7}$=7.2 Hz, J$_{7,8}$=8.5 Hz, 1H, H7); 7.93-7.96 (m, 2H, H2',6'); 8.29 (dd, J$_{5,6}$=7.5 Hz, J$_{5,7}$=1.5 Hz, 1H, H5), $^{13}$C NMR (100.5 MHz, CDCl$_3$); δ 78.13 (2C, CH$_2$Ph); 119.13, 124.86, 126.23, 127.22, 128.90, 129.36, 129.48, 129.62, 130.06, 131.03, 132.29, 135.06, 157.03, 157.10 (25C, Ar); 136.89 (1C, J$_{C,P}$=8.0 Hz, C—O-phosphate); 173.87 (1C, C=O). $^{31}$P NMR (161.8 MHz, CDCl$_3$); δ −7.45 (s, P=O). Anal. Found: C, 69.81; H, 4.60; C$_{29}$H$_{23}$O$_6$P requires C, 69.88; H, 4.65%. HRMS (ESI$^+$) m/z 521.1126, C$_{29}$H$_{23}$NaO$_6$P [M+Na]$^+$ requires 521.1130].

3-Hydroxyflavone-3-phosphate disodium salt

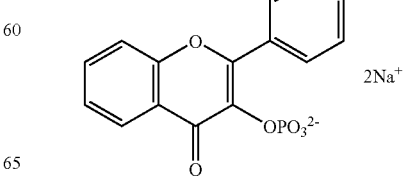

A solution of 3-(dibenzyloxyphosphoryloxy)flavone (2.05 g, 4.09 mmol) and palladium on carbon (10%, 0.25 g) in EtOH:water (4:1. 250 mL) was treated with $H_2$ at atmospheric pressure for 3.5 h. The reaction mixture was filtered (Celite) and the filtrate treated with NaOH (0.50 g in 100 mL water). The aqueous mixture was concentrated under reduced pressure then crystallized from water/acetone to yield the phosphate as pale yellow crystals (1.03 g, 87% yield). $^1$H NMR (499.7 MHz, $D_2O$) δ 7.33 (dd, 1H, $J_{5,6}$=8.0 Hz, $J_{5,7}$=1.2 Hz, H6); 7.40-7.46 (m, 3H, H3', 4', 5'); 7.52 (d, 1H, $J_{7,8}$=8.5 Hz, H8); 7.64 (ddd, 1H, $J_{5,7}$=1.2 Hz, $J_{6,7}$=7.5 Hz, $J_{7,8}$=8.5 Hz, H7); 7.97 (dd, 1H, $J_{5,6}$=8.0 Hz, $J_{5,7}$=1.2 Hz, H5); 8.10 (m, 2H, H2', 6'). $^{13}$C NMR (100.5 MHz, $D_2O$) δ 118.29, 122.92, 124.97, 125.06, 128.50, 129.15, 130.92, 131.33, 134.22, 155.06, 156.68 (13C, Ar); 136.11 (1C, $J_{C,P}$=6.8 Hz, C—O—P); 177.15 (1C, C=O). $^{31}$P NMR (161.8 MHz, $D_2O$) δ 2.98 (s, P). Anal.: Found: C, 49.68; H, 2.51; $C_{15}H_{11}Na_2O_6P$ requires C, 49.74; H, 2.50%.

4'-(Benzyloxy)-3-(dibenzyloxyphosphoryloxy)flavone

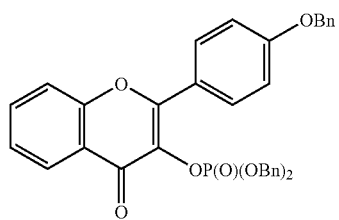

1H-Tetrazole (483 mg, 6.89 mmol) was added to a mixture 4'-benzyloxy-3-hydroxyflavone (1.00 g, 2.72 mmol), dibenzyl N,N-diisopropylphosphoramidite (1.5 mL, 1.6 g, 4.4 mmol) in dichloromethane (30 mL) and the reaction was stirred at rt for 2 h. Additional dibenzyl N,N-diisopropylphosphoramidite (1.0 mL, 1.1 g, 1.5 mmol) was added and the reaction stirred for a further 1 h. The reaction mixture was then cooled to −78° C. and m-CPBA (3.00 g, 12.1 mmol, 70% w/w) was added. The reaction was then warmed to rt and stirred for 45 min. The organic layer was washed with 0.25 M $Na_2S_2O_3$ (×3), sat $NaHCO_3$ (×3), brine (×3), dried ($MgSO_4$) and concentrated. The residue was purified by flash chromatography (50% EtOAc/petrol) to give a yellow solid, which was recrystallized from EtOAc/petrol to afford the phosphate as a colourless solid (1.01 g, 58%); mp 101° C.; $^1$H NMR (500 MHz, $CDCl_3$) δ 5.02 (s, 2H, $CH_2$Ph), 5.16 (s, 2H, $CH_2$Ph), 5.17 (s, 2H, $CH_2$Ph), 6.97 (app. d, 2H, J=8.8 Hz, H3',5'), 7.29-7.36 (m, 15H, 3×Ph), 7.41 (t, 1H, $J_{5,6}$=$J_{6,7}$=8.0 Hz, H6), 7.51 (d, $J_{7,8}$=8.5 Hz, H8), 7.68 (dd, 1H, $J_{6,7}$=8.0, $J_{7,8}$=8.5 Hz, H7), 7.96 (app. d, 2H, J=8.8, H2',6'), 8.30 (dd, 1H, $J_{7,8}$=8.5, $J_{6,8}$=1.5 Hz, H8); $^{13}$C NMR (100 Hz, $CDCl_3$) δ 69.9, 70.0 ($CH_2$), 144.7, 117.9, 122,3, 123.7, 125.0, 126.1, 127.4, 127.8, 128.2, 128.4, 128.7, 130.7, 133.8, 135.8, 135.9, 136.1, 155.2, 155.7, 161.0 (Ar), 172.6 (1C, C=O); $^{31}$P NMR (162 MHz, $CDCl_3$) δ −5.3 (s, P); IR 3063, 3031, 1647, 1601, 1506, 983 $cm^{-1}$; Anal. Found C, 72.60; H, 5.05%, $C_{36}H_{29}O_7P$ requires C, 71.52; H, 4.83%.

Flavone-3-phosphate disodium salt

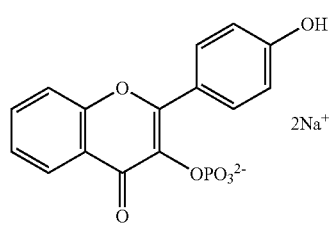

A mixture of 4'-(benzyloxy)-3-(dibenzyloxyphosphoryloxy)flavone (1.00 g, 1.65 mmol) and $Pd(OH)_2$ (120 mg) in THF (10 mL) and water (15 mL) was treated with hydrogen for 3 d. The mixture was filtered (Celite) and the pad washed with THF and water, and the filtrate was concentrated. The solid residue was dissolved in THF (20 mL) and water (10 mL) and triethylamine (600 μL, 4.3 mmol) added and stirred at rt for 30 min. The mixture was concentrated and the residue was dissolved in water. Insoluble material was removed by filtration and the solution passed through an ion exchange column. The eluant was concentrated to afford a solid, which was recrystallised from acetone/water to afford the phosphate as a brown solid (226 mg, 36%); mp 182-184° C.; $^1$H NMR (500 MHz, $D_2O$) δ 7.07 (app. d, 2H, J=8.5 Hz, H3',5'), 7.62 (t, 1H, $J_{5,6}$=$J_{6,7}$=7.5 Hz, H6), 7.72 (d, $J_{7,8}$=8.5 Hz, H8), 7.92 (t, 1H, $J_{6,7}$=$J_{7,8}$=7.5 H7), 8.18 (d, 1H, $J_{5,6}$=7.5 Hz, H5), 8.19 (app. d, 2H, J=8.5, H2',6'); $^{13}$C NMR (100 MHz, $D_2O$) δ 118.4, 122.5, 122.6, 124.9, 125,3, 131.2, 134.4, 155.0, 157.1, 157.2, 158.5 (Ar), 176.3 (1C, C=O); $^{31}$P NMR (162 MHz, $CDCl_3$) δ 0.60 (s, P); IR 3281, 1597, 1579, 1542, 1393, 903 $cm^{-1}$; HRMS (ESI$^-$) m/z 333.0160, $C_{15}H_{10}O_7P$ [M+H]$^-$ requires 333.0159.

4'-(Benzyloxy)-3-(trimethylammoniumylpropylcarbonyloxy)flavone chloride

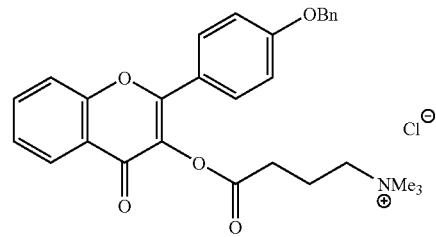

A mixture of carboxypropyltrimemylammonium chloride (0.5 g, 2.7 mmol) and thionyl chloride (2 mL), 3.26 g, 27 mmol) was stirred at room temperature overnight. The solvent was evaporated and the residue dissolved in nitrobenzene (2 mL) and 4'-benzyloxyflavonol (344 mg, 1.00 mmol) was added. The solution was stirred at room temperature for 30 min, then at 65 C for 5 h. The nitrobenzene was removed under reduced pressure (80 C water bath) and the residue was purified by flitration through a plug of silica (7:2:1 EtOAc: MeOH:$H_2O$). The residue was washed with THF and recrystallized from ethanol/pet spirits to afford a yellow powder (30 mg); $^1$H NMR (399.7 MHz, $CDCl_3$) δ 2.01-2.13 (2H, m, $CH_2$), 2.78 (2H, d, J6.8 Hz, $CH_2$), 3.09 (9H, s, $NMe_3$), 3.25-3.35 (2H, m, $CH_2$N), 5.21 (2H, m, $CH_2$Pb), 7.24 (2H, app. d, J9.2 Hz, H2',6'), 7.33-7.49 (m, 5H, Ph), 7.54 (1H, dd, J 8.0, 8.0 Hz, H6), 7.81 (1H, d, $J_{7,8}$8.4 Hz, H8), 7.88 (1H, d, J8.0, 8.4 Hz, H7), 7.92 (2H, app. d, J9.2 Hz, H3',5'), 8.07 (1H, d, $J_{5,6}$ 8.0 Hz, H5).

4'-(Hydroxy)-3-(trimethylammoniumylpropylcarbonyloxy)flavone chloride

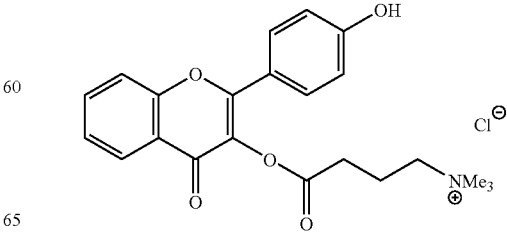

A mixture of the flavone (30 mg) and Pd/C (5%, 5 mg) in EtOH (5 mL) was stirred under an atmosphere of hydrogen for 2 h. The mixture was filtered and the solvent evaporated to afford a yellow solid.

Vasorelaxant and Antioxidant Activity of Flavonoid Derivatives

Effect of Flavonoid Derivatives on $Ca^{2+}$-Induced Contraction

To determine the effect of flavonoids on responses to the influx of extracellular $Ca^{2+}$, contractile responses to exogenous application of $Ca^{2+}$ were examined in the presence of flavonoids in $Ca^{2+}$-free high-$K^+$ solution (60 mM, KPSS). Aortic rings were initially equilibrated at a resting tension of 1 g in normal $Ca^{2+}$-free PSS for 45 minutes. The bath medium was then replaced with $Ca^{2+}$-free KPSS for 45 minutes to determine a reference contraction to $Ca^{2+}$ ($3\times10^{-3}$ M). Following a 30 minute re-equilibration period with $Ca^{2+}$-free PSS, the cumulative contractile responses to $Ca^{2+}$ ($10^{-5}$–$3\times10^{-3}$ M) were determined in KPSS in the presence of a range of concentrations ($10^{-8}$-$10^{-4}$ M) of vehicle, 3',4'-dihydroxyflavonol, 3-hydroxyflavone-3-hemiadipate, 3',4'-dihydroxy-3-hemiadipate, 3-hydroxyflavone-3-phosphate. A 20 minute incubation period was allowed for the flavonoids before examining the responses to $Ca^{2+}$.

Relaxation by Flavonoid Derivatives

Following testing of endothelial integrity, rings were repeatedly washed and re-equilibrated for 30 minutes before the addition of PE ($10^{-8}$–$2\times10^{-7}$ M) and 9,11-dideoxy-9$_\alpha$, 11$_\alpha$-epoxymethano-prostaglandin $F_{2\alpha}$ (U46619, $10^{-9}$-$10^{-8}$ M) to produce an active force in the range of 40-60% of KPSS-induced contraction. The level of precontraction was matched between the various groups by adjusting the concentrations of PE and U46619. Cumulative concentration-response curves in the range $10^{-8}$-$10^{-4}$ M were conducted for 3',4'-dihydroxyflavonol, 3-hydroxyflavone-3-hemiadipate, 3',4'-dihydroxy-3-hemiadipate, 3-hydroxyflavone-3-phosphate.

Experiments were conducted in the presence of an esterase, butyryl cholinesterase (BuCHE, 1000 U/L) for the hemiadipate derivates and a phosphatase 1000 U/L) in the case of the phosphate derivatives.

Effects of Flavonoid Derivatives on Superoxide Levels in an In Vitro Assay

Superoxide anion production in rat isolated aortic segments was determined using lucigenin chemiluminescence. Aortic rings were prepared as described above and then placed in ice-cold Krebs-(N-[2-Hydroxyethyl]piperazine-N'-[2-ethanesulfonic acid] (HEPES buffer) (composition (mM); NaCl 99.0, KCl 4.7, $KH_2PO_4$ 1.0, $MgSO_4 \cdot 7H_2O$ 1.2, D-glucose 11.0, $NaHCO_3$ 25.0, $CaCl_2 \cdot 2H_2O$ 2.5, Na-HEPES 20.0). Aortic rings were pre-incubated for 45 minutes at 37° C. with a pH 7.4, in Krebs-HEPES buffer containing diethylthiocarbamic acid (DETCA, $10^{-3}$ M) to inactivate superoxide dismutase and β-nicotinamide adenine dinucleotide phosphate (NADPH, $10^{-4}$ M) as a substrate for NADPH oxidase and either 3',4'-dihydroxyflavonol ($10^{-4}$ M) as a positive control, vehicle, 3-hydroxyflavone-3-hemiadipate, 3',4'-dihydroxy-3-hemiadipate, 3-hydroxyflavone-3-phosphate ($10^{-8}$-$10^{-4}$ M). Background photon emission was measured for 12 cycles in a 96-well Optiplate containing 0.3 ml per well of Krebs-HEPES buffer together with lucigenin ($5\times10^{-5}$ M) and vehicle or flavonoid ($10^{-8}$-$10^{-4}$ M). Each cycle was counted every one minute. After background reading was completed the incubated aortic rings were transferred to the appropriate wells and photon emission was recounted as described above. The tissue was then placed in a 65° C. oven for 48 hours to allow superoxide production to be normalised to dry tissue weight.

Effects of Flavonoid Derivatives on Superoxide Levels in an In Vitro Assay in the Presence or Absence of an Esterase The effects of vehicle, 3',4'-dihydroxyflavone-3-hemiadipate (21) (DiOHF3HA, $10^{-8}$ M-$10^{-4}$ M) and DiOHF ($10^{-4}$ M) in the presence and absence of Butyryl cholinesterase (BuCHE), 100, 300 and 1000 U/L) on the level of superoxide anions generated in rat isolated aortic segments in the presence of NADPH was expressed as a percentage of control. The method used was as described above except for the addition of the butyryl cholinesterase.

Effects of Flavonoid Derivatives on Superoxide Levels in an In Vitro Assay in the Presence or Absence of a Phosphatase The effect of vehicle, 3-hydroxyflavone-3-phosphate ($10^{-8}$ to $10^{-4}$ M) in the presence or absence of phosphatase (1000 U/L) on the level of superoxide anions generated in rat aorta in the presence of NADPH expressed as a percentage of control was determined as described above for the 3',4'-dihydroxyflavone-3-hemiadipate. A measurable effect on the superoxide anion generation was observed using the 3-hydroxyflavone-3-phosphate in the absence of the phosphatase. This was thought to occur due to the presence of natural phosphatases in the isolated rat tissue.

In Vivo Study of the Effects of Flavonoid Derivatives on the Vascular Function of a Rat A unit dosage of an aqueous solution of 3-hydroxyflavone-3-hemiadipate (15) was administered to a group of male anesthetized Sprague Dawley rats intravenously and the blood pressure monitored over a period of time.

A significant reduction in the blood pressure of rats was observed which is indicative of the in vivo vasorelaxation caused by the flavonoid derivative. No effect was observed when an aqueous solution was administered to a second group of rats.

The experiment was repeated with aqueous solutions of the other synthesized flavonoid derivatives which also resulted in distinct reductions in the blood pressures of the rats.

Screening for Activity and Pharmacokinetics

Preparation of Rat Aorta

The descending thoracic aorta from rats was rapidly dissected and placed in Krebs-bicarbonate solution. Superficial connective tissue and fat surrounding the aorta was removed and the aorta was cut into segments of 2-3 mm length and mounted in organ baths.

Effect of Flavonoids on ACh and SNP Relaxation

After wash out and re-equilibration for 30 min, the aortic rings were then submaximally precontracted with PE and U46619, which were used to produce an active tension of 45-60% of the KPSS-induced maximum contraction. When investigating the effects of the flavonoids, flavonol, flavone-3-hemiadipate (F3HA), 3', 4'-dihydroxyflavone, 3',4'-dihydroxyflavonol, 3',4'-dihydroxyflavone-3-hemiadipate (DiOHF3HA), and flavone-3-phosphate (F3P) on vasorelaxant responses, rings were incubated with one of the compounds for 20 mins before they were precontracted submaximally, followed by a cumulative-concentration response curve to ACh (100 nM-10 μM) or SNP (10 μM-1 μM). In experiments using F3P 1000U/L phosphatase was used in some experiments to cleave the phosphate. Some experiments were conducted in the presence and absence of butyryl cholinesterase (BuCHE, 1000 U/L) to cleave the adipate in DiOHF3HA and F3HA.

Effect of Flavonols and Flavones on PE-Induced Contraction

Rings were incubated for 20 minutes with DiOHF3HA at a range of concentrations ($10^{-7}$-$10^{-4}$ M) or vehicle (0.1% dimethyl sulphoxide, DMSO). A concentration response curve to PE ($10^{-9}$-$10^{-5}$ M) in endothelium-intact (EI) aortic rings was then performed. Experiments were conducted in the presence and absence of BuCHE (1000 U/L) to cleave the adipate in DiOHF3HA.

Effect of Flavonols on $Ca^{2+}$-Induced Contraction

To determine the effect of flavonoids on responses to the influx of extracellular $Ca^{2+}$, contractile responses to exogenous application of $Ca^{2+}$ were examined in the presence of flavonoids in $Ca^{2+}$-free high-$K^+$ solution (60 mM, K+-PSS). Aortic rings were initially equilibrated at a resting tension of 1 g in $Ca^{2+}$-free PSS for 45 minutes. The bath medium was then replaced with $Ca^{2+}$-free K+-PSS for 45 minutes to determine a reference contraction to added $Ca^{2+}$ (3 mM). Following a 30 minute re-equilibration period with $Ca^{2+}$-free PSS, the cumulative contractile responses to $Ca^{2+}$ ($10^{-5}$–$3\times10^{-3}$ M) were determined in $K^+$ PSS in the presence of vehicle (0.1% DMSO), or a range of concentrations ($10^{-7}$-$10^{-4}$ M) of 3'-hydroxyflavonol, F3HA, DiOHF3HA or F3P. A 20 minute incubation period was allowed for the flavonoids before examining the responses to $Ca^{2+}$. Experiments were conducted in the presence and absence of BuCHE (1000 U/L) to cleave the adipate in F3HA and DiOHF3HA. In experiments using F3P, phosphatase (1000 U/L) was used in some experiments to cleave the phosphate.

Relaxation by Flavonoids

Following testing of endothelial integrity, rings were repeatedly washed and re-equilibrated for 30 minutes before the addition of PE ($10^{-8}$–$2\times10^{-7}$ M) and 9,11-dideoxy-$9_\alpha$, $11_\alpha$-epoxymethano-prostaglandin $F2_\alpha$ (U46619, $10^{-9}$-$10^{-7}$ M) to produce an active force in the range of 40-60% of KPSS-induced contraction. Cumulative concentration-response curves in the range $10^{-7}$-$10^{-4}$ M were conducted for vehicle, 3'-hydroxyflavonol, F3HA, DiOHF3HA, F3P. Experiments were conducted in the presence and absence of 1000 U/L BuCHE to cleave the adipate in F3HA and DiOHF3HA. In experiments using F3P 1000 U/L phosphatase was used in some experiments to cleave the phosphate.

Effect of Flavonols and Flavones on Vasorelaxation to ACh in the Presence of Oxidative Stress Control cumulative relaxation responses to ACh were compared with those obtained from endothelium-intact aortic rings treated with pyrogallol ($2\times10^{-5}$ M). The effects of vehicle (0.1% DMSO), phosphatase (1000 U/L) or F3P ($10^{-6}$-$10^{-4}$ M) on responses to ACh in the rat isolated aortic rings exposed to pyrogallol ($2\times10^{-5}$ M) were also determined. Pyrogallol was added when the aortic rings had reached a stable level of contraction with PE and U44619 at a level between 50 and 70% of KPSS-induced tension and 10 minutes was allowed before determining the cumulative concentration-response curves to ACh. In some experiments using F3P 1000 U/L phosphatase was used to cleave the phosphate.

Effect of DiOHF3HA and F3P in Anesthetized Rats

Male Sprague-Dawley rats (250-350 g) were anaesthetised with pentobarbitone sodium (60 mg $kg^{-1}$, ip). The trachea was isolated and cannulated with polyethylene tracheal tube (I.D. 2.0 mm), and the rat was allowed to breathe spontaneously.

Measurements of Arterial Pressure and Heart Rate

The right carotid artery was cannulated and connected with a heparinised saline filled cannula (O.D. 0.75, I.D. 0.58 mm) and connected to a pressure transducer. Mean and phasic arterial pressure were continuously measured and recorded on a polygraph. The heart rate, was derived from the phasic arterial pressure using a tachometer.

Antioxidant and Vascular Effects of Flavonol and Dihydroxyflavone

Flavonol and dihydroxyflavone (DiOHFne) caused concentration dependent decreases in superoxide levels generated by rat aortic rings. At the highest concentration tested (0.1 mM) flavonol and DiOHFne both reduced the superoxide levels to 36±3% of control. Flavonol did not affect the relaxant effects of ACh or SNP. DiOHFne caused concentration-dependent relaxation of rat aorta which was weaker than the effect of DiOHF. Flavonol caused concentration dependent decreases in calcium-induced contraction of rat aortic rings which were relatively weak in comparison to previous observations with DiOHF.

Antioxidant and Vascular Effects of Flavone-3-Hemiadipate (F3HA)

F3HA ($10^{-7}$ M-$10^{-4}$ M) had no inhibitory effect on superoxide generation by rat aorta but the presence of butyryl cholinesterase (BuCHE, 100-1000 U/ml) caused a concentration dependent increase in the inhibitory effect of F3HA (FIG. 6). F3HA only inhibited contractile responses to increasing concentrations of extracellular calcium at the highest concentration tested (0.1 mM).

Antioxidant and Vascular Effects of Dihydroxy Flavone-3-Hemiadipate (DiOHF3HA).

Figure 11:
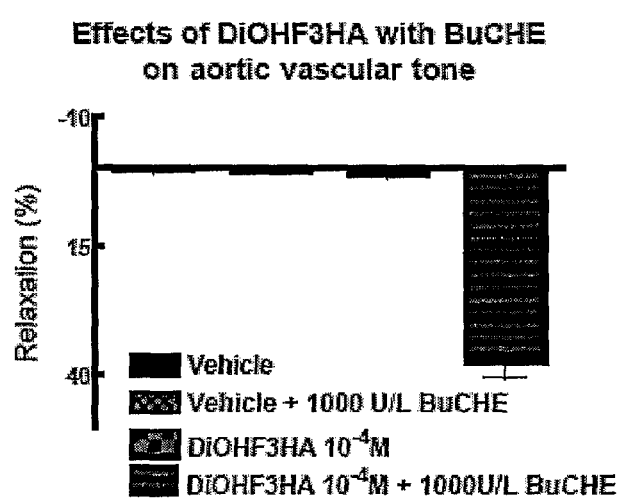
FIG. 11 illustrates the direct relaxing effect of vehicle, 1000U/L BuCHE, DiOHF3HA ($10^{-4}$ M), DiOHF3HA ($10^{-4}$ M) plus 1000 U/L BuCHE. vehicle, 1000 U/L BuCHE and DiOHF3HA ($10^{-4}$ M) had no effect on PE precontracted vessels. DiOHF3HA ($10^{-4}$ M) plus 1000 U/L BuCHE had a marked effect on vascular tone in rat aorta precontracted with PE.

DiOHF3HA ($10^{-7}$ M-$10^{-4}$ M) had no inhibitory effect on superoxide generation by rat aorta but the presence of butyryl cholinesterase (BuCHE, 1000 U/ml) revealed a concentration dependent inhibitory effect. DiOHF3HA alone had no effect on relaxant responses to ACh or SNP. In contrast, in the presence of BuCHE (1000 U/ml) DiOHF3HA significantly increased the sensitivity of the relaxant response to SNP. Similarly DiOHF3HA alone had little effect on calcium-induced contraction of rat aorta, but in the presence of BuCHE (1000 U/ml) DiOHF3HA (0.1 mM) had an equivalent inhibitory effect to DiOHF. This suggests that when the adipate was removed by the esterase the hemiadipate was equally active to the parent DiOHF. DiOHF3HA was also found to cause direct relaxation of pre-contracted rat aortic rings only in the presence of the esterase (FIG. 11).

Figure 12:
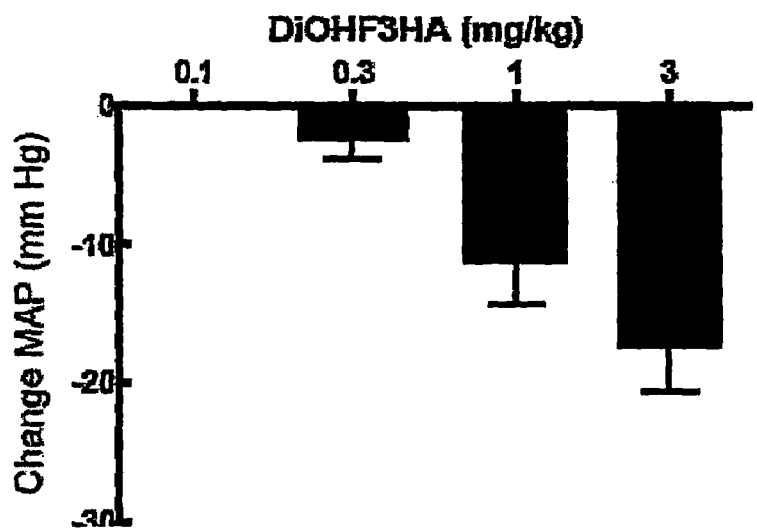
FIG. 12(a) illustrates the dose-dependent decrease in MAP (mm Hg) indicating vasodilatation in response to DiOHF3HA in anaesthetised rats.
FIG. 12(b) illustrates the dose-dependent decrease in HR (beats/min) in response to DiOHF3HA.
Figure 12:
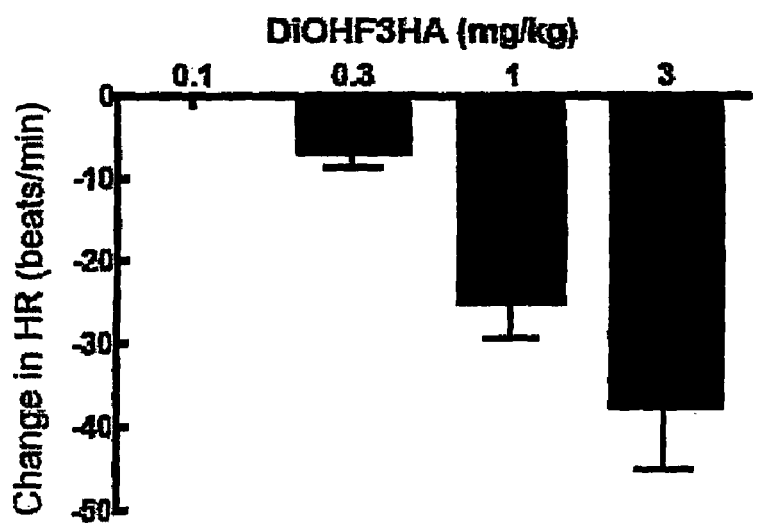
Figure 13:
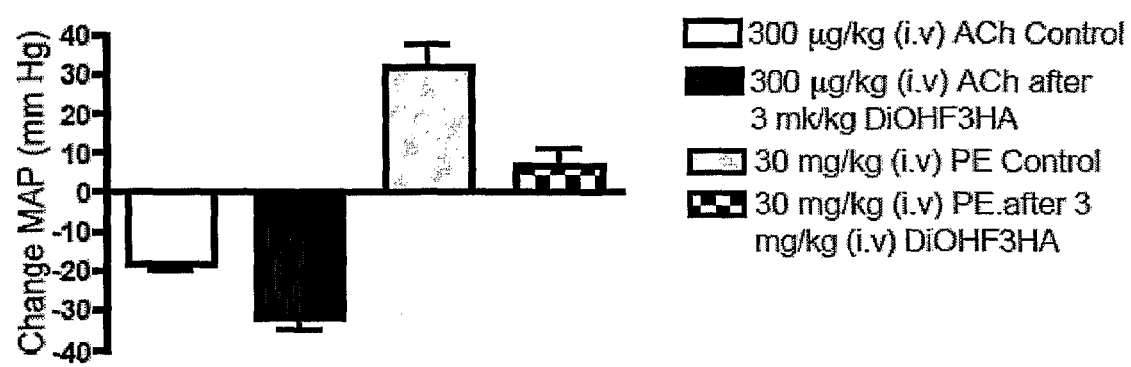
FIG. 13 illustrates the decrease in MAP (mm Hg) indicating vasodilatation in response to ACh in anaesthetised rats, dilator response to ACh was enhanced by 30 min pre-treatment with 3 mg/kg DiOHF3HA. A increase in MAP (mm Hg) indicating vasoconstriction in response to PE in anaesthetised rats, constrictor responses to PE were diminished by 30 min pre-treatment of 3 mg/kg DiOHF3HA.
Figure 14:
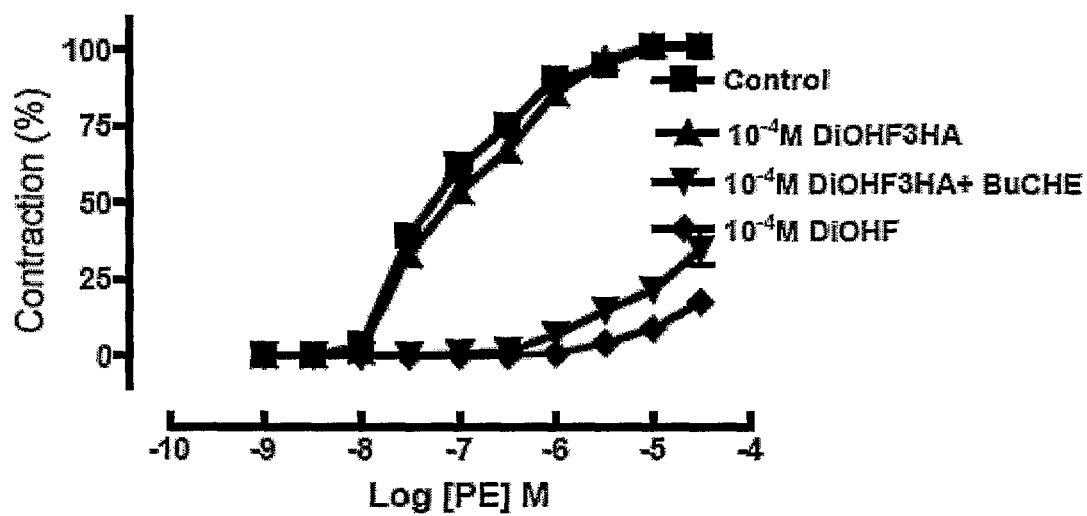
FIG. 14 illustrates the concentration response curves to PE generated in the presence of control, DiOHF3HA with and without BuCHE and DiOHF in rat aortic rings. DiOHF3HA in the presence of BuCHE and DiOHF both appeared to inhibit the response to PE in a concentration dependent manner.

DiOHF3HA (0.1, 0.3, 1.3 mg/kg) was injected intravenously, allowing at least 30 min between injections, and the peak changes in mean arterial pressure and heart rate measured. DiOHF3HA caused dose-dependent decreases in arterial pressure (FIG. 12a) and heart rate (FIG. 12b). In a separate group of experiments ACh (0.3 mg/kg iv) and phenylephrine (PE, 30 mg/kg iv) were injected before and 30 minutes after DiOHF3HA (3 mg/kg iv), a time when arterial pressure and heart rate had returned to control levels. DiOHF3HA significantly enhanced the depressor response to ACh and attenuated the PE-induced increase in arterial pressure (FIG. 13).

In rat aortic rings DiOHF3HA (0.1 mM), in the absence or presence of cholinesterase, had no effect on endothelium-dependent relaxation in response to the calcium ionophore A23187 or to isoprenaline. DiOHF3HA (0.1 mM) given alone had no effect on PE-induced contraction but caused marked inhibition in the presence of esterase. The level of inhibition was similar to that observed in response to the presence of the same concentration (0.1 mM) of DiOHF.

Antioxidant and Vascular Effects of Flavone-3-Phosphate (F3P)

F3P or phosphatase (1000 U/l) had no effect on superoxide generation by rat aortic segments whereas F3P caused a concentration-dependent inhibition of superoxide levels in the presence of phosphatase. F3P, in the presence of phosphatase, increased the sensitivity of rat aortic rings to relaxation by ACh but not SNP. Oxidant stress, caused by the presence of pyrogallol ($2×10^{-5}$ M), significantly reduced the maximum response to ACh but the response was restored by the presence of F3P plus phosphatase. Responses to SNP were unaffected by any of those treatments, F3P caused a small inhibition of calcium-induced contraction but the effect was significantly enhanced by the presence of phosphatase.

F3P (0.1, 0.3, 1, 3, 10 mg/kg) was injected intravenously, allowing at least 30 minutes between injections, and the peak changes in mean arterial pressure and heart rate measured (FIG. 16a). DiOHF3HA caused dose-dependent decreases in arterial pressure and heart rate (FIG. 12a and 12b) but the depressor response was small compared to DiOHF (1 mg/kg iv).

Summary

These studies involved an assessment of the vascular and antioxidant activity of flavonols, 3',4'-dihydroxyflavone (DiOHFne), 3',4'-dihydroxyflavonol (DiOHF), flavone-3-hemiadipate (F3HA), 3',4'-dihydroxy flavone-3-hemiadipate (DiOHF3HA) and flavone-3-phosphate.

Flavone-3-hemiadipate (F3HA) alone had no antioxidant or vascular activity when applied alone but the presence of a cholinesterase to cleave the adipate substitution revealed the ability of F3HA to inhibit calcium-induced contraction.

Dihydroxy flavone-3-hemiadipate (DiOHF3HA) had no antioxidant or vascular activity when applied alone but the presence of a cholinesterase to cleave the adipate substitution revealed the ability of DiOHF3HA to inhibit superoxide levels produced by rat aorta, to inhibit calcium-induced contraction and to cause direct relaxation of rat aortic rings. In the presence of the esterase the level of activity of DiOHF3HA was similar to DiOHF. In the anaesthetized rat DiOHF3HA caused concentration dependent decreases in arterial pressure and heart rate.

Flavone-3-phosphate (F3P) alone had no antioxidant or vascular activity but the presence of a phosphatase to cleave the phosphate substitution revealed the ability of F3P to inhibit superoxide levels produced by rat aorta, to inhibit calcium-induced contraction and to enhance endothelium-dependent relaxation in the presence of oxidant stress. In the presence of the phosphatase the level of activity of F3P was similar to DiOHF. In the anaesthetized rat F3P caused only small concentration dependent decreases in arterial pressure and heart rate. The effects were much smaller than seen with DiOHF.

Cardioprotective of 3',4'-dihydroxy flavonol adipate (DiOHF3HA) following myocardial ischaemia reperfusion The ability of the synthetic flavonol, 3',4' dihydroxy flavonol adipate (DiOHF3HA) to prevent myocardial ischaemia and reperfusion injury in anaesthetised Sheep was assessed. Unlike the parent compound DiOHF, the adipate derivative was soluble in aqueous solution, particularly water.

DiOHF3HA administered in aqueous solution caused a dose-related reduction in infarct size, which was similar to that caused by a similar molar dose of DiOHF when dissolved in DMSO.

Intravenous DiOHF3HA infusion did not alter haemodynamic indices (arterial blood pressure, heart rate, left ventricular-end diastolic pressure (LV-EDP).

Since DiOHF3HA caused an equivalent degree of cardioprotection to the parent compound following cardiac ischaemia-reperfusion injury In anaesthetised sheep, these data support the hypothesis that this novel derivative compound is effectively converted to the parent compound in vivo.

Surgical Preparation

Five groups of anaesthetised adult merino sheep (35-45 kg wethers) were examined:
(1) Control (n=5)
(2) DiOHF (2 mg/kg, n=2)
(3) DiOHF3HA (2.7 mg/kg, n=3)
(4) DiOHF (5 mg/kg, n=3)
(5) DiOHF3HA (6.6 mg/kg, n=4).

Anaesthesia was induced by intravenous thiopentone sodium (15 mg/kg) and following tracheal intubation was maintained by isoflurane (1.5-2%). A catheter was inserted in the right facial artery for arterial blood sampling and monitoring arterial pressure. Intravenous infusions were made via a catheter inserted into the jugular vein. The heart was exposed through a left thoracotomy performed at the fourth intercostal space. A 4F catheter-tipped manometer was inserted through the left atrium into the left ventricle to measure left ventricular pressure (LVP). An additional silastic cannula was inserted into the left atrial appendage for the injection of lignocaine and for infusion of Evans Blue. The left anterior descending coronary artery (LAD) was dissected from the epicardium immediately distal to its second diagonal branch, and a transit-time 2 mm flow probe was placed around it to monitor the LAD blood flow. A silk suture was passed under the LAD proximal to the probe and both ends of the silk were threaded through a plastic tube to form a vascular snare.

Experimental Design

The animals were allowed to stabilise for 10-15 minutes after the completion of the surgical procedure. Sheep were then randomly divided into different treatment groups. All sheep had 30 minute baseline recording followed by 1 hour ischaemia and 3 hours reperfusion.

During the course of the experiment, haemodynamic measurements were recorded at 5 minute intervals and blood samples were taken at designated time-points. After 30 minutes of ischaemia, flavonol treatment was administered. DiOHF was dissolved in 2 ml DMSO plus 14 ml polyethylene glycol:water (1:1). DiOHF3HA was dissolved in 20 ml 0.1M $Na_2CO_3$. The drugs were given at 1 ml/min i.v. The two doses of DiOHF3HA (2.7 mg/kg and 6.6 mg/kg) were chosen to achieve equivalent molar doses to the parent DiOHF compound (at 2 mg/kg and 5 mg/kg, respectively). Control animals did not receive any intravenous solutions. Lignocaine was used, as required, to ameliorate arrhythmias.

Determination of the Area at Risk and Infarct Size

The area of myocardium at risk and infarct size were delineated by Evan's blue and triphenyltetrazolium chloride (TTC) staining. After 3 hours of reperfusion, the LAD was re-occluded at the original occlusion site. Immediately after intravenous injection of pentobarbitone (100 mg $kg^{-1}$) to arrest the heart, Evan's blue dye (1.5%, 40 ml) was injected into the left atrium to define the myocardium at risk. The heart was rapidly removed and the left ventricle was sliced into transverse sections about 1 cm thick. The unstained risk area was traced onto the same transparencies. The sections were then incubated in 0.1 M sodium phosphate buffer containing 1% TTC for 20 min (37° C., pH 7.4). The infarcted area was traced onto transparencies. The area of myocardium at risk, and infarct size, were measured by computerised planimetry. The former was expressed as a percentage of total left ventricular volume (AR/LV %) and infarct size was expressed as a percentage of the area of myocardium at risk (IS/AR %).

Plasma Markers for Myocardial Infarction

Arterial blood samples (5 ml) were collected into chilled heparinised tubes at baseline, during ischaemia and at three time points during the reperfusion period (1 hour, 2 hour and 3 hour). Following centrifugation at 4° C., plasma samples were stored at −20° C. until measurement to determine levels of lactate dehydrogenase and creatinine kinase.

Results

In the following summary of results, myocardial infarct size in the 5 different treatment groups is reported. Given the effectiveness of the highest dose of DiOHF3HA, changes in all other parameters are only reported with respect to the Control group of animals versus the DiOHF3HA (6.6 mg/kg) group of animals.

In the Control group, one of the sheep died due to ventricular fibrillation in the first 10 minutes of reperfusion. Thus, control data are based on n=4 sheep.

Myocardial Infarct Size

In this study, the area of left ventricle subjected to ischaemia (AR) among the 5 different treatment groups of sheep was similar, (11%-20%, FIG. 17, left panel). In contrast, the infarct size, normalised to the AR, was smaller in the DiOHF and DIOHF3HA treated groups compared to control animals (FIG. 17, right panel). Specifically, the infarct size normalized to the area at risk (IS/AR) was reduced from 83±4% in controls to 49±8% by DiOHF3HA (6.7 mg/kg) and to 47±8% by DiOHF (5 mg/kg). With the lower doses of DiOHF3HA (2.7 mg/kg) and DiOHF (2 mg/kg) IS/AR was 64% and 73%, respectively.

LAD Flow

Baseline LAD flow was similar in the Control and DiOHF3HA (6.6 mg/kg) groups of sheep (7-9 ml/mm). During ischaemia, LAD flow fell to zero in all animals. During the early stage of reperfusion, coronary hyperperfusion occurred in all sheep. Generally, this transient increase in LAD flow returned to baseline levels after 30-60 mins of reperfusion. The regression of flow appeared to be more rapid in the DiOHF3HA group.

Haemodynamic Response to Ischaemia/Reperfusion

Baseline arterial pressure was not different between the two groups of sheep (average over 30 mins, ~80 mmHg). In contrast, resting HR was lower (P<0.05) in the control sheep (90±4 bpm) compared to the DiOHF3HA-treated sheep (105±3 bpm). This difference remained throughout the course of the experiment. Both MAP and HR were unchanged during the 20-min infusion period of DiOHF3HA administration. Moreover, no marked change in arterial pressure or HR was observed in either group of sheep during myocardial ischaemia and reperfusion.

Resting LV-EDP was not different between the two groups of sheep (~11 mmHg) but the maximal positive value of the first derivative of LVP ($dP/dt_{max}$) was lower (P<0.05) in the control sheep (1454±62 mmHg/s) compared to DiOHF3HA-treated sheep (1967±103 mmHg/s). This difference remained throughout the course of the experiment. Both LV-EDP and $dP/dt_{max}$ were unchanged during the 20-min infusion period of DiOHF3HA administration. Moreover, no marked change in LV-EDP and $dP/dt_{max}$ was observed in either group of sheep during myocardial ischaemia reperfusion. Haemodynamic benefits of the drug showed up more clearly after 24 hours of reperfusion.

In anaesthetized sheep, following 1 hour ischaemia and 3 hours reperfusion, plasma lactate dehydrogenase increased by 227±141 U/L in the control group (n=3) and by 67±32 U/L in the group treated with DiOHF3HA (n=4). In these sheep plasma creatine kinase increased by 2411±958 U/L in the control group and by 1579±936 U/L in the group treated with DiOHF3HA.

Recovery from Ischaemic Stroke in Rats Using Synthetic Flavonoids

Plasma Markers for Myocardial Infarction

Ischaemic stroke was studied in conscious rats, with daily monitoring of neurological function and post mortem morphological assessment of cerebral infarcts at 72 hours alter stroke. Unilateral, transient cerebral ischaemia and reperfusion was induced in conscious rats by injection of the potent vasoconstrictor endothelin-1 outside but close to the right middle cerebral artery MCA, (via a pre-implanted guide tube). The ensuing stroke was graded on a scale of 0 to 5 by immediate behaviour, and potential neuroprotective compounds were injected intravenously 3 h after the stroke, and at 24 hour intervals thereafter.

Surgical Preparation

Male Hooded Wistar rats (280-340 g) were anaesthetised with pentobarbitone sodium in a volume of 0.6 ml (60 mg/kg i.p.) for insertion of an intravenous (i.v.) catheter into the jugular vein for acute drug administration, A 23-gauge stainless steel guide cannula was then stereotaxically implanted into the piriform cortex 2 mm dorsal to the right MCA (0.2 mm anterior, −5.2 mm lateral and −5.9 mm ventral). The cannula was secured with dental acrylate cement and two small screws inserted into the skull. The scalp was closed with sutures. Rats were housed individually on a 12 h day/night cycle at a temperature of 18-22° C. and allowed to recover for 5 days before induction of stroke.

Stroke Induction

Vaso constriction of the right middle cerebral artery (MCA) was induced in conscious rats by administration of the potent vasoconstrictor agent endothelin-1 (ET-1) (60 pmol in 3 µl of saline over 10 min) via a 30-gauge injector that protruded 2 mm beyond the end of the previously implanted stereotaxic guide cannula. The injector was held in place by a poly-tubing cuff and the rat was placed in a clear Plexiglass box for observation during ET-1 injection. During stroke induction we observed counter-clockwise circling, clenching and dragging of the contralateral forepaw, validating the correct placement of the cannula. These behavioural changes occurred within 2 to 10 minutes of the commencement of the ET-1 injection and similar behaviours have been reported by other researchers employing this model. We have assigned a rating scale of stroke severity based on these behavioural changes during stroke and have shown that vehicle-treated rats assigned with higher stroke ratings have greater infarct volumes and neurological deficits. Rats that did not display any behavioural change were deemed not have had a stroke and were excluded from the study. Sham-injected rats underwent cannula implantation but did not receive any ET-1 injection. Rectal temperatures were taken with a thermistor probe, prior to stroke and at 30- or 60-minute intervals for 3 hours after stroke.

Assessment of Functional Outcome

All behavioural tests were conducted prior to any procedures (pre-surgery, day 1), immediately prior to ET-1-induced MCA occlusion (pre-ischemia, day 6) and 24, 48 and 72 hours after ET-1-induced MCA occlusion. The behaviour of each rat was compared to pre-stroke, thus each rat acted as its own control. All rats were coded so that the investigator was blinded to treatment condition. Neurological abnormalities were evaluated with the use of a neurological deficit score based on detection of abnormal posture and hemiplegia. Abnormal pastures were assessed by suspending rats by the tail and scoring twisting of the thorax and extension of the forelimbs. Hemiplegia was evaluated when rats were placed on a raised platform. Deficits were deemed to be present when the hind limb contralateral to the infarcted hemisphere slipped off the edge of the platform and/or when the contralateral forelimb slipped off when the snout and whiskers were not in contact with the surface. All behaviours were scored on the following scale: 0=no deficit; 1=slight; 2=moderate; and 3=severe. Thus, when scores were totalled the maximum neurological deficit score was 12. A score of 0 was considered normal.

Sensory hemi-neglect was evaluated using a test consisting of placing adhesive tapes (Avery adhesive label, 100 mm diameter circles) on the distal-radial region of each wrist, Placement of the first tape was randomised between contralateral and ipsilateral limbs. The tape on both forepaws was touched simultaneously prior to placing the animal in a plexiglass cage and measuring with a stopwatch, both the latency to touch and the latency to remove each stimulus from the contralateral and ipsilateral forepaws were recorded. The test was terminated at 180 seconds if tapes had not already been removed.

Drug Treatment

All compounds were given intravenously as a single bolus dose 3 hours post-stroke at a concentration which yielded 37 μmol/kg. Vehicle controls were also used and were specific for each compound. After the first dose 3 hours post-stroke, the animals were injected once daily with either drug, or vehicle at 24 and 48 h. The total injection volume for each compound was approximately 300 μl for a 300 g rat, with a 200 μl straight saline flush to ensure full drug administration.

Quantification of Ischemic Damage

Rats were decapitated 72 h after ischemia and their brains were removed and frozen in liquid nitrogen and stored at −80° C. Coronal cryostat sections (16 μm) were cut at eight predetermined coronal planes throughout the brain from −3.2 to 6.8 mm relative to Bregma. Infarct was measured in triplicate unstained sections based on the observation that damaged areas in unstained slide-mounted brain sections are visible to the naked eye as clearly defined frosted or dark areas, while normal tissue is essentially translucent. By applying the principle of ballistic light propagation and using a simple apparatus combined with a computerised image analysis system, the unstained slide mounted section showing damaged areas was clearly visible on the monitor. Light passes directly through the transparent, undamaged tissue to the camera, whereas light rays are diffracted by the damaged tissue. The areas of damage can then easily be outlined, selected and recorded using the image analysis system. Total infarct volume was calculated by integrating the cross-sectional area of damage at each stereotaxic level with the distances between levels. The influence of edema on the infarct area was corrected by applying the following formula: (area of normal hemisphere/area of infarcted hemisphere) x area of infarct. Slides were also coded so that the investigator was blinded to treatment condition.

Stroke Rating

Rats showed neurological behavioural deficits indicative of stroke within 2-10 minutes of ET-1 injection but not after an equal volume of saline alone. These deficits included specific behavioural responses such as clenching and failure to extend the contralateral forepaw, and circling in the direction contralateral to the occlusion. Grooming behaviour preceded circling and was observed in almost all rats. Grooming occurred in a stereotypical manner with facial grooming being followed by full body grooming in one continuous movement. Other behaviours such as teeth chattering, biting of the cage and bedding or tongue poking, were observed less frequently. These behavioural responses observed at the time of stroke could be ranked based on their degree and severity. We have also shown that there is a positive correlation between stroke rating and neurological deficit score and stroke rating and infarct volume, in vehicle treated rats (n=40). Following ranking, stroke rats were paired based on equal stroke rating so that stroke ratings were evenly distributed between vehicle and Drug treatment groups. These rats were then coded so that the remaining assessments could be performed blind to treatment.

Stratifying Drug Treatment

Prognostic models are used to predict functional outcome and survivability in human stroke patients in order to support clinical management of stroke patients and to correctly stratify treatment groups in clinical trials. The use of similar models in experimental stroke animals has not previously been attempted. In the ET-1 model of MCA occlusion it is possible to observe behavioural responses during stroke induction and assign a rating scale of stroke severity based on these responses. Therefore it is possible to predict which animals will have severe strokes and which animals will have mild to moderate strokes. This process also allows for some predication of the area of risk, which is potentially salvageable by neuroprotective agents after stroke. Severe strokes leave little area of risk for neuroprotection given that the infarct occupies greater the 70% of total hemisphere volume. Mild to moderate strokes however reveal a greater area of risk for salvage, and therefore present a greater opportunity for neuroprotection. Indeed clinical MRI studies in patients are now being used to stratify patients in a similar manner in order to determine who is more likely to benefit from future drug treatment. For this reason we removed animals that had severe stroke ratings of 4 or 5 at the end of drug treatment analysis, and re-analysed data in mild to moderate stroke groups (ratings 1-3) for all future compounds tested.

3',4'-Dihydroxyflavonol (DiOHF)

Initial experiments conducted in our laboratory assessed the delayed neuroprotective potential of DiOHF (10 mg/kg) given intravenously 3 hours post-stroke onset. Each rat received 3 bolus doses of DiOHF dissolved in 20% DMSO, 40% Polyethylglycol and 40% sterile water for injection. 3',4'-Dihydroxyflavonol (DiOHF) administration in rats with modest strokes (scores 2-3, n=6 and 5, compound and . vehicle, respectively) reduced the neurological deficits at 48 and 72 h, and abolished the increase in hemineglect scores ("sticky tape test") after stroke, that were observed in the control rats given endothelin plus drug vehicle alone. Importantly, DiOHF reduced the volume of infarct produced in the cerebral cortex, and completely prevented an infarct developing in the striatum of the brain.

DiOHF (10 mg/kg) treatment in mild to moderate stroke rats significantly reduced the area of infarct throughout the cortex and the striatum compared with vehicle treatment. DiOHF treatment also significantly improved neurological outcome in mild to moderate stroke rats, in comparison to vehicle treated rats.

3',4'-Dihydroxyflavone-3-Hemiadipate (DiOHF3HA) for Treatment of Stroke

Each rat received 3 bolus doses of DiOHF3HA (15 mg/kg/day i.v.) dissolved in a $Na_2CO_3$ buffered saline (0.1M, pH 7.8) for injection.

| Vehicle | DiOHF3HA |
|---|---|
| Grade #2 (n = 3) | #2 (n = 1) |
| Grade #3 (n = 4) | #3 (n = 4) |
| Grade #4 (n = 7) | #4 (n = 6) |

Following stroke, there was no significant weight loss in either treatment group. Core temperature prior to stroke in both treatment groups was within normal physiological limits. Following stroke there was a significant increase in temperature at 30 minutes in both treatment groups, however temperature returned to within normal levels after this time. Following intravenous injection of vehicle or DiOHF3HA, temperature appeared to increase in both treatment groups but this was not significantly different from pre-stroke temperature.

Following stroke rats in both treatment groups exhibited significantly higher neurological deficit scores 24, 48 and 72 hours post-stroke when compared to pre-stroke scores. Treatment with DiOHF3HA (15 mg/kg/day) measurably improved neurological deficit scores at 24, 48 or 72 hours post-stroke when compared with vehicle treated rats. Vehicle treated rats showed increased latency to remove sticky labels from the stroke affected contralateral forepaw when compared with the ipsilateral side (P<0.05, two-way RM-ANOVA with 2-factor repetition, hours after stroke and side). This effect was abolished after treatment with DiOHF3HA (15 mg/kg/day).

Infarct area through the cortex was significantly reduced following treatment with DiOHF3HA (15 mg/kg i.v.) when compared with vehicle.

In summary, DiOHF3HA (15 mg/kg) treatment significantly improved neurological function in the hemineglect test, and also reduced the area of damage in the striatum following stroke compared with vehicle treatment.

Effect of DiOHF3HA in Mild to Moderate Strokes

A selected group of rats were studied with mild to moderate strokes.

| Vehicle | DiOHF3HA |
|---|---|
| Grade #3 (n = 4) | #2 (n = 1) |
| Grade #4 (n = 3) | #3 (n = 4) |

Rats did not lose weight following mild to moderate stroke in either treatment group. Core temperature prior to stroke in both treatment groups was within normal physiological limits. Following mild to moderate stroke there was a significant increase in temperature at 30 minutes in both treatment groups, but temperature returned to within normal levels after this time.

Following mild to moderate strokes, rats in both treatment groups exhibited significantly higher neurological deficit scores pre-stroke and 24, 48 and 72h post-stroke when compared to pre-surgery scores. Treatment with DiOHF3HA (15 mg/kg/day) had no effect on neurological deficit scores when compared with vehicle treated rats. Vehicle treated rats with mild to moderate strokes showed an increased latency to touch sticky labels from the stroke affected contralateral forepaw when compared with the Ipsilateral side, at 24 and 48 hours (P<0.05, two-way RM-ANOVA with 2-factor repetition, h after stroke and side). Vehicle treated rats also showed an increased latency to remove sticky labels at 24 hr (P<0.05, two-way RM-ANOVA with 2-factor repetition, hours after stroke and side). These effects were abolished following treatment with DiOHF3HA (15 mg/kg/day) (FIG. 18).

Infarct area in mild to moderate stroke rats through the cortex was significantly reduced following treatment with DiOHF3HA (15 mg/kg i.v. per day) when compared with vehicle (FIG. 19). DiOHF3HA treatment also significantly reduced the area of infarct through the striatum.

In summary, DiOHF3HA (15 mg/kg) treatment in mild to moderate stroke rats significantly reduced the area of infarct through the cortex and the striatum compared with vehicle treatment DiOHF3HA treatment also significantly restored neurological function in the hemineglect test.

Unless otherwise indicated, all values in graphs are means with s.e. mean shown by vertical lines.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of the general formula I:

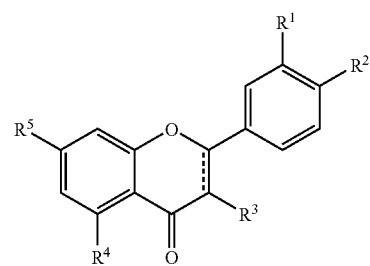

wherein:

═ denotes a single or double bond; and $R^1$, $R^2$, $R^3$, $R^4$, $R^5$ are independently selected from H, OH or a group according to formula (Ia):

—O-L-D-E     (Ia)

wherein:

O is oxygen;

i) L is a C═O group, D is an alkylene group with a chain length equivalent to about 1 to 20 carbon atoms, and E is a substituted or unsubstituted carboxylic acid group; or ii) L and D are absent and E is an ester group according to formula (Ic):

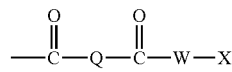

wherein:

Q is a substituted or unsubstituted alkylene;

W is O; and X is H, a substituted or unsubstituted alkyl, benzyl, or a mono- or divalent cationic salt, or an ammonium cationic salt;

provided that at least one of $R^1$, $R^2$, $R^3$, $R^4$, $R^5$ is other than H or OH;

with the proviso that the compound is not 3,3',4',7-Tetra-O-benzylquercetin 5-[1,4,5,6-tetra-O-benzyl-2-O-(dibenzyl-oxyphosphoryl)-myo-inositol 3-succinate]; 3',4',7-Tri-O-benzylquercetin 3-[1,4,5,6-tetra-O-benzyl-2-O-(dibenloxyphosphoryl) myo-inositol 3-succinate]; Quercetin 5-(2-O-phosphono-myo-inositol 1-succinate) and Quercetin 3-(2-O-phosphono-myo-inositol 1-succinate).

2. A compound according to claim 1, wherein the $R^4$ and $R^5$ are both H.

3. A compound according to claim 1, wherein $R^1$ and $R^2$ are both OH.

4. The compound according to claim 1, wherein ═ denotes a double bond, L and D are absent and E is an ester group according to the formula (Ic):

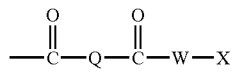

(Ic)

wherein

Q is a substituted or unsubstituted alkylene;

W is O; and X is H, a substituted or unsubstituted alkyl, benzyl, or a mono- or divalent cationic salt, or an ammonium cationic salt.

5. The compound according to claim 1, wherein Q is substituted or unsubstituted $C_1$ to $C_6$ alkylene.

6. The compound according to claim 1, wherein X is H and Q is a butlyene group.

7. The compound according to claim 1, wherein
═ denotes a double bond;
$R^4$ and $R^5$ are H;
$R^1$ and $R^2$ are OH;
L and D are absent and E is an ester group according to formula (Ic):

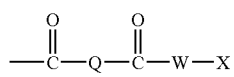

(Ic)

wherein:

Q is a substituted or unsubstituted alkylene;

W is O; and X is H, a mono- or divalent cationic salt, or an ammonium cationic salt.

8. The compound of claim 7, wherein Q is substituted or unsubstituted $C_1$ to $C_6$ alkylene.

9. The compound according to claim 7, wherein X is H and Q is a butylene group.

10. The compound according to claim 1, wherein
═ denotes a double bond;
$R^1$, $R^2$ and $R^4$ are H;
$R^3$ and $R^5$ are independently selected from H, OH or a group according to formula (Ia):

—O-L-D-E     (Ia)

wherein

O is oxygen;

i) L is a C═O group, D is an alkylene group with a chain length equivalent to about 1 to 20 carbon atoms, and E is a substituted or unsubstituted carboxylic acid group, or ii) L and D are absent and E is an ester group according to formula (Ic):

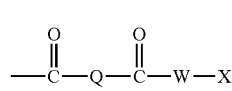

(Ic)

wherein

Q is a substituted or unsubstituted alkylene;

W is oxygen; and X is H, a substituted or unsubstituted alkyl, benzyl, or a mono- or divalent cationic salt, or an ammonium cationic salt;

provided that at least one of $R^3$ and $R^5$ is other than H or OH.

11. The compound according claim 10, wherein L and D are absent and E is an ester group according to formula (Ic):

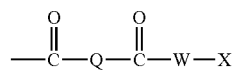

(Ic)

wherein

Q is a substituted or unsubstituted alkylene;

W is oxygen; and X is H, a substituted or unsubstituted alkyl, benzyl, or a mono- or divalent cationic salt, or an ammonium cationic salt.

12. The compound according to claim 11, wherein Q is substituted or unsubstituted $C_1$ to $C_6$ alkylene.

13. The compound according to claim 11, wherein X is H and Q is a butylene group.

14. The compound according to claim 1 which is

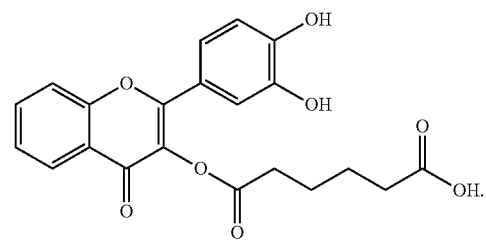

15. The compound according to claim 1 which is

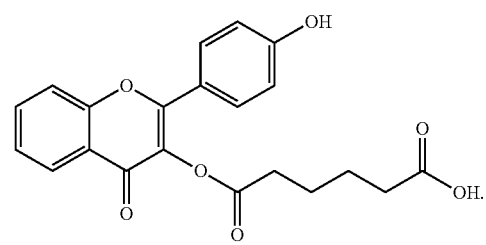

16. A compound selected from the group comprising 3-(Benzyloxycarbonylbutylcarbonyloxy)flavone; 3-Hydroxyflavone 3-hemiadipate; 4'-(Benzyloxy)-3-(benzyloxycarbonylbutylcarbonyloxy)flavone; 4'-Hydroxyflavone 3-hemiadipate; 3',4'-Dibenzyloxy-3-(benzyloxycarbonylbutylcarbonyloxy)flavone; 3',4'-Dihydroxyflavone 3-hemiadipate; 3,4'-Di-(benzyloxycarbonylbutylcarbonyloxy)flavone;

flavone 3,4'-bis(hemiadipate); 3,7-Di-(benzyloxycarbonyl-butylcarbonyloxy)flavone; 3,7-bis(hemiadipate)flavone; 4'-Hydroxy-3-Hydroxyflavone-3-quaternary ammonium ester.

17. A pharmaceutically and/or veterinary composition comprising a pharmaceutically and/or veterinarily acceptable carrier or diluent together with a compound according to claim 1.

18. A method of treating a disease(s) in a subject associated with the presence of reactive oxidative species (ROS), the method comprising;
   administering an effective amount of at least one compound according to claim 1.

19. The method according to claim 18, wherein the subject in need of such treatment is at risk of developing ischaemia.

20. The method according to claim 18, wherein the subject is suffering ischaemia and/or reperfusion injury as a result of an acute or chronic condition.

21. The method according to claim 18, wherein the disease is selected from cerebrovascular disease, pulmonary vascular disease, atherosclerosis, artery disease, congestive heart disease, coronary disease, peripheral vascular disease, diabetes, hypertension, migraine, chronic obstructive pulmonary disease and retinal vascular disease.

22. The method according to claim 18, wherein the disease is selected from stroke, myocardial infarction, mechanical trauma resulting from crush injury or surgery.

23. The method according to claim 18, wherein the disease is the result of vascular surgery.

24. The method according to claim 18, wherein the disease is the result of heart bypass and/or transplant surgery.

25. The method according to claim 18, wherein the compound is administered to the subject before and/or during the surgery.

26. The method according to claim 18, wherein the compounds is administered to the subject orally.

27. The method according to claim 18, wherein the compound is

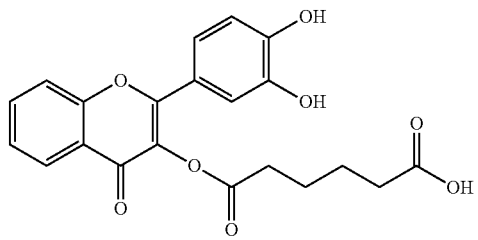

or its pharmaceutically acceptable salt.

28. A method of slowing the progression of atherosclerosis and/or coronary heart disease in a subject comprising:
   administering an effective amount of at least one compound according in claim 1.

29. The method according to claim 28, wherein the compound is

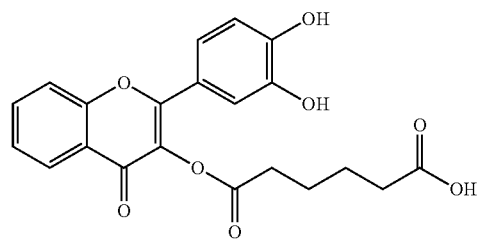

or its pharmaceutically acceptable salt.

30. A method of at least ameliorating the damage to a subject caused by ischaemia and/or reperfusion injury, the method comprising:
   administering an effective amount of at least one compound according to claim 1.

31. The method according to claim 30, wherein the compound is

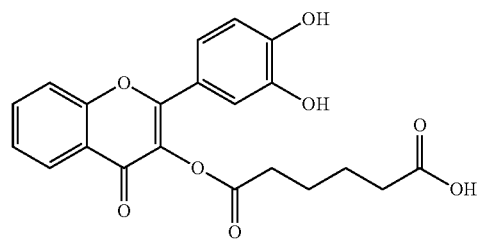

or its pharmaceutically acceptable salt.

32. A method of at least ameliorating damage to a subject caused by the administration of a therapeutic agent, the method comprising co-administrating to a subject:
   i) a therapeutic agent; and
   ii) administering an effective amount of at least one compound according to claim 1.

33. The method according to claim 32, wherein the therapeutic agent is an oxidative therapeutic agent.

34. The method according to claim 32, wherein the therapeutic agent is anti-cancer agent.

35. The method according to claim 32, wherein the therapeutic agent is anthracycline and homologues thereof.

36. The method according to claim 32, wherein the compound is

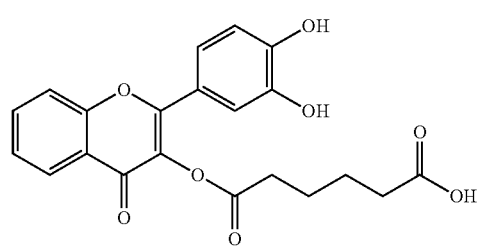

or its pharmaceutically acceptable salt.

* * * * *

UNITED STATES PATENT AND TRADEMARK OFFICE
CERTIFICATE OF CORRECTION

PATENT NO.        : 8,017,649 B2  
APPLICATION NO.   : 11/885736  
DATED             : September 13, 2011  
INVENTOR(S)       : Jarrott et al.

Page 1 of 1

It is certified that error appears in the above-identified patent and that said Letters Patent is hereby corrected as shown below:

ON THE TITLE PAGE:

Item "(73) Assignee", please insert --NeuProtect Pty Ltd., Victoria (AU)--.

Signed and Sealed this  
Seventh Day of August, 2012

David J. Kappos  
*Director of the United States Patent and Trademark Office*